United States Patent
Kaib et al.

(10) Patent No.: US 10,960,221 B2
(45) Date of Patent: Mar. 30, 2021

(54) SECURE LIMITED COMPONENTS FOR USE WITH MEDICAL DEVICES

(71) Applicant: ZOLL Medical Corporation, Chelmsford, MA (US)

(72) Inventors: Thomas E. Kaib, Irwin, PA (US); Shane S. Volpe, Saltsburg, PA (US); Ernast Sevo, Pittsburgh, PA (US)

(73) Assignee: ZOLL Medical Corporation, Chelmsford, MA (US)

( * ) Notice: Subject to any disclaimer, the term of this patent is extended or adjusted under 35 U.S.C. 154(b) by 0 days.

(21) Appl. No.: 16/277,050

(22) Filed: Feb. 15, 2019

(65) Prior Publication Data
US 2019/0175929 A1    Jun. 13, 2019

Related U.S. Application Data

(62) Division of application No. 15/233,245, filed on Aug. 10, 2016, now Pat. No. 10,252,070.
(Continued)

(51) Int. Cl.
*A61N 1/39* (2006.01)
*A61N 1/02* (2006.01)
(Continued)

(52) U.S. Cl.
CPC .......... *A61N 1/3975* (2013.01); *A61B 5/0432* (2013.01); *A61B 5/7475* (2013.01);
(Continued)

(58) Field of Classification Search
CPC .... A61N 1/3975; A61N 1/3925; A61N 1/025; A61N 1/09; A61N 1/3904; A61B 5/0432;
(Continued)

(56) References Cited

U.S. PATENT DOCUMENTS

| 4,576,170 A | 3/1986 | Bradley et al. |
| 4,580,572 A | 4/1986 | Granek et al. |

(Continued)

FOREIGN PATENT DOCUMENTS

| EP | 707825 A2 | 4/1996 |
| EP | 761255 A1 | 3/1997 |

(Continued)

OTHER PUBLICATIONS

American Journal of Respiratory and Critical Care Medicine, vol. 166, pp. 111-117 (2002), American Thoracic Society, ATS Statement: Guidelines for the Six-Minute Walk Test, available at http://ajrccm.atsjournals.org/cgi/content/ull/166/1/111.

(Continued)

*Primary Examiner* — Paula J Stice
(74) *Attorney, Agent, or Firm* — Finch & Maloney PLLC

(57) ABSTRACT

In some examples, an ambulatory medical device is provided. The ambulatory medical device includes at least one sensor configured to acquire data descriptive of the patient, one or more processors in communication with the at least one sensor, a patient care component executable by the one or more processors, and a limited functionality component executable by the one or more processors. The patient care component is configured to perform one or more primary operations of the ambulatory medical device at least in part by accessing the data descriptive of the patient. The limited functionality component is configured to exchange information with a communication device and to not affect the one or more primary operations of the ambulatory medical device.

27 Claims, 12 Drawing Sheets

Related U.S. Application Data

(60) Provisional application No. 62/215,558, filed on Sep. 8, 2015.

(51) Int. Cl.
  *A61B 5/00* (2006.01)
  *A61B 5/0432* (2006.01)
  *A61B 5/0245* (2006.01)
  *A61B 7/00* (2006.01)
  *A61B 5/1455* (2006.01)

(52) U.S. Cl.
  CPC .............. *A61N 1/025* (2013.01); *A61B 5/002* (2013.01); *A61B 5/0245* (2013.01); *A61B 5/14551* (2013.01); *A61B 7/003* (2013.01); *A61N 1/3904* (2017.08)

(58) Field of Classification Search
  CPC ......... A61B 5/7475; A61B 5/00; A61B 5/002; A61B 5/0245; A61B 5/14551; G06F 3/0619; G06F 3/065; G06F 3/0689
  See application file for complete search history.

(56) References Cited

U.S. PATENT DOCUMENTS

| | | |
|---|---|---|
| 4,583,547 A | 4/1986 | Granek et al. |
| 4,729,377 A | 3/1988 | Granek et al. |
| 4,928,690 A | 5/1990 | Heilman et al. |
| 4,991,217 A | 2/1991 | Garrett et al. |
| 5,078,134 A | 1/1992 | Heilman et al. |
| 5,381,798 A | 1/1995 | Burrows |
| 5,741,306 A | 4/1998 | Gleyak et al. |
| 5,929,601 A | 7/1999 | Kaib et al. |
| 5,944,669 A | 8/1999 | Kaib |
| 6,065,154 A | 5/2000 | Rulings et al. |
| 6,097,982 A | 8/2000 | Gleyak et al. |
| 6,253,099 B1 | 6/2001 | Oskin et al. |
| 6,280,461 B1 | 8/2001 | Gleyak et al. |
| 6,336,900 B1 | 1/2002 | Alleckson et al. |
| 6,374,138 B1 | 4/2002 | Owen et al. |
| 6,406,426 B1 | 6/2002 | Reuss et al. |
| 6,418,346 B1 | 7/2002 | Nelson et al. |
| 6,442,433 B1 | 8/2002 | Linberg |
| 6,546,285 B1 | 4/2003 | Owen et al. |
| 6,602,191 B2 | 8/2003 | Quy |
| 6,681,003 B2 | 1/2004 | Linder et al. |
| 6,694,191 B2 | 2/2004 | Starkweather et al. |
| 6,804,554 B2 | 10/2004 | Ujhelyi et al. |
| 6,889,078 B2 | 5/2005 | Struble et al. |
| 6,889,079 B2 | 5/2005 | Bocek et al. |
| 6,908,437 B2 | 6/2005 | Brardy |
| 7,088,233 B2 | 8/2006 | Menard |
| 7,149,579 B1 | 12/2006 | Koh et al. |
| 7,340,296 B2 | 3/2008 | Stahmann et al. |
| 7,453,354 B2 | 11/2008 | Reiter et al. |
| 7,476,206 B2 | 1/2009 | Palazzolo et al. |
| 7,488,293 B2 | 2/2009 | Marcovecchio et al. |
| 7,712,373 B2 | 5/2010 | Nagle et al. |
| 7,831,303 B2 | 11/2010 | Rueter et al. |
| 7,974,689 B2 | 7/2011 | Volpe et al. |
| 7,991,460 B2 | 8/2011 | Fischell et al. |
| 8,121,683 B2 | 2/2012 | Bucher et al. |
| 8,140,154 B2 | 3/2012 | Donnelly et al. |
| 8,271,082 B2 | 9/2012 | Donnelly et al. |
| 8,319,632 B1 | 11/2012 | Vaisnys et al. |
| 8,369,944 B2 | 2/2013 | Macho et al. |
| 8,406,842 B2 | 3/2013 | Kaib et al. |
| 8,644,925 B2 | 2/2014 | Volpe et al. |
| 8,649,861 B2 | 2/2014 | Donnelly et al. |
| 8,676,313 B2 | 3/2014 | Volpe et al. |
| 8,706,215 B2 | 4/2014 | Kaib et al. |
| 8,774,917 B2 | 7/2014 | Macho et al. |
| 8,880,196 B2 | 11/2014 | Kaib |
| 8,897,860 B2 | 11/2014 | Volpe et al. |
| 8,904,214 B2 | 12/2014 | Volpe et al. |
| 9,283,399 B2 | 3/2016 | Donnelly et al. |
| 2001/0031991 A1 | 10/2001 | Russial |
| 2002/0181680 A1 | 12/2002 | Linder et al. |
| 2003/0004547 A1 | 1/2003 | Owen et al. |
| 2003/0032988 A1 | 2/2003 | Fincke |
| 2003/0095648 A1 | 5/2003 | Kaib et al. |
| 2003/0212311 A1 | 11/2003 | Nova et al. |
| 2005/0131465 A1 | 6/2005 | Freeman et al. |
| 2005/0202843 A1 | 9/2005 | Fors et al. |
| 2005/0246199 A1 | 11/2005 | Futch |
| 2006/0211934 A1 | 9/2006 | Hassonjee et al. |
| 2007/0239214 A1 | 10/2007 | Cinbis |
| 2008/0033495 A1 | 2/2008 | Kumar |
| 2008/0058884 A1 | 3/2008 | Matos |
| 2008/0097793 A1 | 4/2008 | Dicks et al. |
| 2008/0249591 A1 | 10/2008 | Gaw et al. |
| 2008/0287749 A1 | 11/2008 | Reuter |
| 2008/0306560 A1 | 12/2008 | Macho et al. |
| 2008/0306562 A1 | 12/2008 | Donnelly et al. |
| 2008/0312709 A1 | 12/2008 | Volpe et al. |
| 2009/0073991 A1 | 3/2009 | Landrum et al. |
| 2009/0076341 A1 | 3/2009 | James et al. |
| 2009/0076342 A1 | 3/2009 | Amurthur et al. |
| 2009/0076343 A1 | 3/2009 | James et al. |
| 2009/0076346 A1 | 3/2009 | James et al. |
| 2009/0076349 A1 | 3/2009 | Libbus et al. |
| 2009/0076350 A1 | 3/2009 | Bly et al. |
| 2009/0076363 A1 | 3/2009 | Bly et al. |
| 2009/0076559 A1 | 3/2009 | Libbus et al. |
| 2009/0146822 A1 | 6/2009 | Soliman |
| 2009/0234410 A1 | 9/2009 | Libbus et al. |
| 2009/0264792 A1 | 10/2009 | Mazar |
| 2009/0292194 A1 | 11/2009 | Libbus et al. |
| 2009/0307266 A1 | 12/2009 | Fleizach et al. |
| 2009/0312650 A1 | 12/2009 | Maile et al. |
| 2010/0022886 A1 | 1/2010 | Ayati et al. |
| 2010/0052892 A1 | 3/2010 | Allen et al. |
| 2010/0069735 A1 | 3/2010 | Berkner |
| 2010/0076533 A1 | 3/2010 | Dar et al. |
| 2010/0298899 A1 | 11/2010 | Donnelly et al. |
| 2010/0312297 A1 | 12/2010 | Volpe et al. |
| 2011/0022105 A9 | 1/2011 | Owen et al. |
| 2011/0170692 A1 | 7/2011 | Konrad et al. |
| 2011/0172550 A1 | 7/2011 | Martin et al. |
| 2011/0288604 A1 | 11/2011 | Kaib et al. |
| 2011/0288605 A1 | 11/2011 | Kaib et al. |
| 2012/0011382 A1 | 1/2012 | Volpe et al. |
| 2012/0112903 A1 | 5/2012 | Kaib et al. |
| 2012/0146797 A1 | 6/2012 | Oskin et al. |
| 2012/0150008 A1 | 6/2012 | Kaib et al. |
| 2012/0158075 A1 | 6/2012 | Kaib et al. |
| 2012/0191476 A1 | 7/2012 | Reid et al. |
| 2012/0278104 A1 | 11/2012 | Traughber et al. |
| 2012/0283794 A1 | 11/2012 | Kaib et al. |
| 2012/0289809 A1 | 11/2012 | Kaib et al. |
| 2012/0293323 A1 | 11/2012 | Kaib et al. |
| 2012/0302860 A1 | 11/2012 | Volpe et al. |
| 2013/0013014 A1 | 1/2013 | Donnelly et al. |
| 2013/0060149 A1 | 3/2013 | Song et al. |
| 2013/0085538 A1 | 4/2013 | Volpe et al. |
| 2013/0144355 A1 | 6/2013 | Macho et al. |
| 2013/0218252 A1 | 8/2013 | Kaib et al. |
| 2013/0231711 A1 | 9/2013 | Kaib |
| 2013/0324868 A1 | 12/2013 | Kaib et al. |
| 2013/0325078 A1 | 12/2013 | Whitting et al. |
| 2013/0325096 A1 | 12/2013 | Dupelle et al. |
| 2014/0004814 A1 | 1/2014 | Elghazzawi |
| 2014/0049377 A1 | 2/2014 | Krusor et al. |
| 2014/0163334 A1 | 6/2014 | Volpe et al. |
| 2014/0206974 A1 | 7/2014 | Volpe et al. |
| 2014/0277243 A1 | 9/2014 | Maskara et al. |
| 2014/0303680 A1 | 10/2014 | Donnelly et al. |
| 2014/0324112 A1 | 10/2014 | Macho et al. |
| 2015/0035654 A1 | 2/2015 | Kaib et al. |
| 2015/0039042 A1 | 2/2015 | Amsler et al. |
| 2015/0039053 A1 | 2/2015 | Kaib et al. |

(56) References Cited

U.S. PATENT DOCUMENTS

| | | |
|---|---|---|
| 2015/0080699 A1 | 3/2015 | Kaib et al. |
| 2015/0224330 A1 | 8/2015 | Kaib et al. |

FOREIGN PATENT DOCUMENTS

| | | | |
|---|---|---|---|
| JP | 2002509472 A | | 3/2002 |
| JP | 2002-514107 A | | 5/2002 |
| JP | 2008-302228 A | | 12/2008 |
| JP | 2008302225 A | | 12/2008 |
| JP | 2009510631 A | | 3/2009 |
| JP | 2009-521865 A | | 6/2009 |
| WO | 83/04171 A1 | | 12/1983 |
| WO | 1997022297 A1 | | 6/1997 |
| WO | 1998039061 A2 | | 9/1998 |
| WO | 2000030529 A1 | | 6/2000 |
| WO | 2004078259 A1 | | 9/2004 |
| WO | 2007019325 A2 | | 2/2007 |
| WO | 2009034506 A1 | | 3/2009 |
| WO | 2009122277 A2 | | 10/2009 |
| WO | 2012006524 A1 | | 1/2012 |
| WO | 2012100219 A1 | | 7/2012 |
| WO | 2013130957 A2 | | 9/2013 |
| WO | 2014097035 A1 | | 6/2014 |

OTHER PUBLICATIONS htto://web.archive.org/web/20030427001846/http:/www.lifecor. comiimagelib/imageproduct.asp. Published by LifeCor, Inc., 2002, on a webpage owned by LifeCor, Inc.

Association for the Advancement of Medical Instrumentation, ANSI/AAMI DF80:2003 Medical Electrical Equipment—Part 2-4: Particular Requirement for the Safety of Cardiac Defibrillators (including Automated External Defibrillators) 2004, ISBN 1-57020-210-9; abstract; p. 50, section 107.1.2.

International Search Report and Written Opinion from PCT/US2013/028598 dated May 9, 2013.

SECURE LIMITED COMPONENTS FOR USE WITH MEDICAL DEVICES

RELATED APPLICATIONS

This application claims the benefit under 35 U.S.C. § 121 as a division of U.S. patent application Ser. No. 15/233,245, titled "SECURE LIMITED COMPONENTS FOR USE WITH MEDICAL DEVICES," filed on Aug. 10, 2016, now U.S. Pat. No. 10,225,070, which claims priority under 35 U.S.C. § 119(e) to U.S. Provisional Application Ser. No. 62/215,558, titled "SECURE LIMITED COMPONENTS FOR USE WITH MEDICAL DEVICES," filed Sep. 8, 2015, both of which are hereby incorporated herein by reference in their entireties for all purposes.

BACKGROUND

This disclosure relates to secure limited components for use with medical devices and systems and techniques for communicating with medical devices through such components.

There are a wide variety of electronic and mechanical devices for monitoring and treating patients' medical conditions. In some examples, depending on the underlying medical condition being monitored or treated, medical devices such as cardiac pacemakers or defibrillators may be surgically implanted or connected externally to the patient. In some cases, physicians may use medical devices alone or in combination with drug therapies to treat patient medical conditions.

One of the most deadly cardiac arrhythmias is ventricular fibrillation, which occurs when normal, regular electrical impulses are replaced by irregular and rapid impulses, causing the heart muscle to stop normal contractions and to begin to quiver. Normal blood flow ceases, and organ damage or death can result in minutes if normal heart contractions are not restored. Because the victim has no perceptible warning of the impending fibrillation, death often occurs before the necessary medical assistance can arrive. Other cardiac arrhythmias can include excessively slow heart rates known as bradycardia.

Implantable or external pacemakers and defibrillators (such as automated external defibrillators or AEDs) have significantly improved the ability to treat these otherwise life-threatening conditions. Such devices operate by applying corrective electrical pulses directly to the patient's heart. For example, bradycardia can be corrected through the use of an implanted or external pacemaker device. Ventricular fibrillation can be treated by an implanted or external defibrillator.

Some medical devices operate by continuously or substantially continuously monitoring the patient's heart through one or more sensing electrodes for treatable arrhythmias and, when such is detected, the device applies corrective electrical pulses directly to the heart through one or more therapy electrodes.

SUMMARY

In some examples, an ambulatory medical device is provided. The ambulatory medical device comprises at least one sensor configured to acquire data descriptive of the patient, one or more processors in communication with the at least one sensor, a patient care component executable by the one or more processors, and a limited functionality component executable by the one or more processors. The patient care component is configured to perform one or more primary operations of the ambulatory medical device at least in part by accessing the data descriptive of the patient. The limited functionality component is configured to exchange information with a communication device and to not affect the one or more primary operations of the ambulatory medical device.

In the ambulatory medical device, the information exchanged with the communication device may comprise one or more commands received from the communication device, and the limited functionality component may be configured to execute the one or more commands. The limited functionality component may be configured to not affect the one or more primary operations of the ambulatory medical device by being configured to be unable to affect the one or more primary operations of the ambulatory medical device. The one or more primary operations of the ambulatory medical device may comprise one or more critical operations of the ambulatory medical device. The one or more critical operations may comprise at least one of monitoring a patient for a predetermined patient condition, providing information relating to the predetermined patient condition to a person, receiving user input relating to the predetermined patient condition from the person, determining a therapy for the patient on detecting the predetermined patient condition, and providing the therapy to the patient based on the predetermined patient condition.

In the ambulatory medical device, the at least one sensor may comprise a sensing electrode, the patient care component is configured to monitor a cardiac function of the patient based on the data acquired by the sensing electrode, and the one or more primary operations of the ambulatory medical device comprise operations relating to detecting a cardiac condition of the patient based on the cardiac function of the patient.

The ambulatory medical device may further comprise at least one treatment electrode configured to provide a defibrillating shock. The at least one sensor may comprise a sensing electrode. The patient care component may be configured to monitor a cardiac function of the patient based on data acquired by the sensing electrode. The one or more primary operations of the ambulatory medical device may comprise operations relating to treating a cardiac condition of the patient via the at least one treatment electrode upon detecting the cardiac condition based on the cardiac function of the patient.

In the ambulatory medical device, the sensor may comprise at least one of a tissue fluid sensor, a heart sounds sensor, a lung sounds sensor, an accelerometer, and a pulse oximeter.

The ambulatory medical device may further comprise a memory. The patient care component may be configured to manipulate primary data stored in the memory and manipulate secondary data stored in the memory. The limited functionality component may be configured to not affect the one or more primary operations of the ambulatory medical device at least in part by being configured to manipulate the secondary data but be limited to read-only access of the primary data.

In the ambulatory medical device, the memory may be configured to provide a primary data store and a secondary data store. The patient care component may be configured to manipulate primary data stored in the primary data store and manipulate secondary data stored in the secondary data store. The limited functionality component may be configured to not affect the one or more primary operations of the ambulatory medical device at least in part by being configured to manipulate data stored in the secondary data store but be limited to read-only access of data stored in the primary data store.

In the ambulatory medical device, the patient care component may be executable by a first processing thread of the one or more processors and the limited functionality component may be executable by a second processing thread of the one or more processors.

In the ambulatory medical device, the memory may be configured to provide a primary data store and a secondary data store. The one or more processors may comprise a primary processor and a secondary processor. The patient care component may be executable by the primary processor. The limited functionality component may be executable by the secondary processor. The patient care component may be configured to manipulate primary data stored in the primary data store and manipulate secondary data stored in the secondary data store. The limited functionality component may be is configured to not affect the one or more primary operations of the ambulatory medical device at least in part by being configured to manipulate data stored in the secondary data store but be limited to read-only access of data stored in the primary data store. The primary processor and the secondary processor may be processing cores of a single physical processor.

In the ambulatory medical device, the limited functionality component may be configured to not affect the one or more primary operations of the ambulatory medical device at least in part by being configured to limit execution of one or more commands received from the communication device. The limited functionality component may be configured to limit execution of the one or more commands to those one or more commands that do not affect the one or more primary operations of the ambulatory medical device. The limited functionality component may be configured to either limit or shut down execution of the one or more commands based at least on one of a threshold number of commands per time period, a threshold number of active streams, a threshold percentage utilization of the at least one processor, a threshold percentage memory consumed, and a threshold number of threads. The limited functionality component may be configured to limit execution of the one or more commands to a threshold based on a type of the at least one processor.

The ambulatory medical device may further comprise a battery for providing battery power to the ambulatory medical device. The limited functionality component may be configured to either limit or shut down execution of the one or more commands upon detecting that an amount of battery power transgresses a threshold value.

In the ambulatory medical device, the limited functionality component may be configured to authenticate the information received from the communication device as originating from one or more previously identified communication devices. The limited functionality component may be configured to authenticate the information received from the communication device using at least one of password authentication and certificate-based authentication.

The ambulatory medical device may further comprise a user interface component. The limited functionality component may be configured to send one or more interface commands to the user interface component. The one or more interface commands may be configured to initiate output of a predefined message via the user interface component. The limited functionality component may be configured to execute an interface command configured to modify a message to be output by the user interface component and send one or more interface commands to the user interface component, the one or more interface commands comprising at least one interface command configured to initiate output of the modified message. The interface command may be configured to not affect the one or more primary operations of the ambulatory medical device at least in part by being configured to determine whether the message can be modified based on identifying whether the message is flagged as restricted from modification by at least the limited functionality component. The limited functionality component may be configured to send one or more interface commands to the user interface component based on the one or more commands received from the communication device.

In the ambulatory medical device, the limited functionality component may be an application program interface implemented using at least one of a representational state transfer, JavaScript object notation, extensible markup language, and encrypted uniform resource locator parameters. The limited functionality component may be accessible by a transmission control protocol socket.

In the ambulatory medical device, at least one command of the one or more commands may be further configured to initiate transmission of information from the ambulatory medical device to the communication device. The at least one command may be configured to initiate transmission of information from the ambulatory medical device to the communication device (a) in response to a predetermined condition, (b) substantially in real time, (c) during an occurrence of the predetermined condition, (d) in response to user input, (e) in response to a predetermined triggering event, (f) continuously over a period of time, (g) substantially continuously over a period of time, (h) during periodic time intervals, or (i) during aperiodic time intervals. The information may be descriptive of at least one of a cardiac function of the patient and a status of the ambulatory medical device. The information may be descriptive of the cardiac function of the patient and may comprise electrocardiogram data. The information may be descriptive of the status of the ambulatory medical device and may comprise electrode fall-off status. The information may comprise at least one of electrocardiogram data, heart sound data, patient location data, ambulatory medical device status data, patient name, and compliance data.

The ambulatory medical device may comprise a wearable cardiac monitor. The ambulatory medical device may comprise a cardiac monitor configured to either continuous or substantially continuous monitor a patient via the at least one sensor and provide a treatment to the patient via one or more therapy electrodes. The ambulatory medical device may comprise a cardiac monitor configured to provide a treatment to the patient via one or more adhesive electrodes.

According to another example, a system is provided. The system comprises a communication device in communication with an external sensor and an ambulatory medical device. The ambulatory medical device comprises at least one sensor configured to acquire data descriptive of the patient, one or more processors in communication with the at least one sensor, a patient care component executable by the one or more processors, and a limited functionality component executable by the one or more processors. The patient care component may be configured to perform one or more primary operations of the ambulatory medical device at least in part by accessing the data descriptive of the patient. The limited functionality component may be configured to execute commands received from the communication device, the limited functionality component configured to not affect the one or more primary operations of the ambulatory medical device.

In the system, the communication device may comprise at least one of another medical device distinct from the ambulatory medical device, a wearable device distinct from the ambulatory medical device, a charger of the ambulatory medical device, a base station of the ambulatory medical device, and a smart phone. The wearable device may comprise at least one of a watch, anklet, necklace, belt buckle, and glasses. The communication device may be in data communication with the ambulatory medical device by either a wired or wireless network connection. The ambulatory medical device may comprises a user interface component. The commands may comprise at least one command configured to receive information descriptive of the communication device and request that the user interface component display the information. The information may describe at least one of an image stored on the communication device, a signal strength of a network connection between the ambulatory medical device and the communication device, and an amount of power remaining in a battery comprised within the communication device. The communication device may be comprised within the ambulatory medical device.

In the system, the communication device may be further configured to generate a first request to execute a first command to configure a threshold value for a patient parameter monitored by the ambulatory medical device and transmit the first request to the limited functionality component. The limited functionality component may be further configured to receive the first request; parse the first request to identify the first command and the threshold value; execute the first command; monitor, in response to executing the first command, the patient parameter to determine whether the patient parameter transgresses the threshold value; and transmit a notification to a recipient device where the patient parameter transgresses the threshold value. The patient parameter may be time elapsed since the patient last complied with a prescribed treatment schedule and the threshold value may be a prescribed time interval within the prescribed treatment schedule. The prescribed treatment schedule may require a rehabilitation session. The prescribed treatment schedule may require taking medication.

In the system, the ambulatory medical device may comprise a user interface component, and the limited functionality component may be further configured to prompt for input indicating whether the patient complied with the prescribed treatment schedule. The patient parameter may be heartbeats per minute (bps) and the threshold value may be 180 bps. The communication device may be further configured to generate a second request to execute a second command to configure an identifier of the recipient device to be an address, and transmit the second request to the limited functionality component. The limited functionality component may be further configured to receive the second request; parse the second request to identify the second command and the address; execute the command; and store, during execution of the second command, the address as the identifier of the recipient device, thereby configuring the limited functionality component to notify the recipient device at the address where the patient's bps transgresses 180 bps. The recipient device may be the ambulatory medical device. The recipient device may be the communication device.

According to another example, a communication device is provided. The communication device comprises memory, at least one processor in data communication with the memory, and a medical device interface component executable by the at least one processor. The medical device interface component is configured to communicate with an ambulatory medical device, the communications comprising commands configured to not affect one or more primary operations of the ambulatory medical device. The communication device may be configured to store medical device data received from the ambulatory medical device in a local storage on the communication device when the communication device is unable to connect to a remote server. The communication device may be configured to transmit the stored medical data to the remote server when a connection with the remote server is established.

According to another example, an ambulatory medical device configured to care for a patient is provided. The ambulatory medical device comprises memory configured to provide a primary data store and a secondary data store; at least one sensing electrode configured to acquire electrocardiogram data descriptive of the patient's cardiac function; at least one treatment electrode configured to provide a defibrillating shock; one or more processors coupled to the memory, the at least one sensor, and the at least one treatment electrode, the one or more processors comprising a primary processor and a secondary processor; a patient care component executable by the primary processor and configured to perform one or more primary operations of the ambulatory medical device at least in part by being configured to access the data descriptive of the patient: manipulate primary data stored in the primary data store; and manipulate secondary data stored in the secondary data store; and a limited functionality component is executable by the secondary processor and configured to not affect the one or more primary operations of the ambulatory medical device at least in part by being configured to manipulate data stored in the secondary data store but be limited to read-only access of data stored in the primary data store.

Implementations can include one or more of the following advantages.

In some implementations, a medical device includes a limited functionality component that provides, to a communication device, limited access to information processed by the medical device. This limited functionality component is designed to provide access without affecting any primary operations performed by the medical device. In some examples, the limited functionality component provides access to medical device information by receiving commands from the communication device relating to the medical device information, executing the commands, and issuing responses to the communication device.

In some examples, the limited functionality component protects the primary operations of the medical device by actively monitoring computing resources utilized by execution of the commands and adjusting the computing resources available for command execution. The limited functionality component may also protect the primary operations by directly limiting the number and/or type of commands executed. In some examples, the limited functionality component avoids impact to the primary operations by executing through computing resources that are isolated from computing resources used to execute primary operations. This isolation may be physical or virtual and may involve any combination of data storage resources, processing resources, and power resources.

Due to the implementation of these techniques, a communication device can safely receive a wide array of preprocessed information from the medical device and use this pre-processed information, without further modification, to inform the patient or care providers of important facts. This communication device may also be in communication with a remote server that is accessible by care providers. In some implementations described in further detail below, such a communication device can be part of the medical device and communicate with the limited functionality component of the medical device. Accordingly, the medical device can directly receive commands from a remote server, execute the commands, and directly issue responses to the remote server.

For instance, in one example, a communication device includes a directed rehabilitation application that is configured to, e.g., monitor a patient wearing a cardiac monitor during exercises, and issue instructions, including instructions to start and stop performing such exercises at specific times. For example, such exercises can be part of a rehabilitation program prescribed for the patient. In such an example, the communication device can be configured to transmit commands to the limited functionality component within the cardiac monitor. These commands can be configured to cause the limited functionality component to notify the communication device if the patient's heart rate exceeds a threshold value or follows a particular trend or pattern over time. Where the communication device receives such a notification, the communication device may issue commands to the limited functionality component instructing the patient to slow down/ramp down a current activity and/or stop. Using the techniques disclosed herein, the cardiac monitor may provide such functionality without affecting the cardiac monitor's primary operations.

In another example, an ambulatory medical device is provided. The ambulatory medical device includes at least one sensor configured to acquire signals descriptive of a patient's cardiac function, the at least one sensor including at least one sensing electrode; at least one processor configured to convert the signals to data descriptive of the patient's cardiac function; at least one patient care component executable by the at least one processor and configured to perform one or more primary operations of the ambulatory medical device at least in part by accessing the data descriptive of the patient, the one or more primary operations including monitoring the patient's cardiac function; and a limited functionality component executable by the at least one processor and configured to exchange information with a communication device, the limited functionality component being configured to not affect the one or more primary operations of the ambulatory medical device.

The information exchanged between the ambulatory medical device and the communication device may include one or more commands received from the communication device and the limited functionality component may be configured to execute the one or more commands. The one or more primary operations of the ambulatory medical device may include monitoring the patient for a predetermined patient condition, providing information relating to the predetermined patient condition to a user interface, receiving user input relating to the predetermined patient condition from the user interface, determining a therapy for the patient on detecting the predetermined patient condition, and providing the therapy to the patient in response to detecting the predetermined patient condition.

In the ambulatory medical device, the at least one sensor may include a sensing electrode; the patient care component may be configured to monitor a cardiac function of the patient based on the data acquired by the sensing electrode; and the one or more primary operations of the ambulatory medical device may include operations relating to detecting a cardiac condition of the patient based on the cardiac function of the patient. The ambulatory medical device may further include at least one treatment electrode configured to provide a defibrillating shock, wherein the one or more primary operations of the ambulatory medical device comprise operations relating to treating a cardiac condition of the patient via the at least one treatment electrode upon detecting the cardiac condition.

The ambulatory medical device may further include a memory. The at least one patient care component may be configured to manipulate primary data stored in the memory; and manipulate secondary data stored in the memory. The limited functionality component may be configured to not affect the one or more primary operations of the ambulatory medical device at least in part by being configured to manipulate the secondary data but be limited to read-only access of the primary data. The memory may be configured to provide a primary data store and a secondary data store. The at least one patient care component may be configured to manipulate primary data stored in the primary data store and manipulate secondary data stored in the secondary data store. The limited functionality component may be configured to not affect the one or more primary operations of the ambulatory medical device at least in part by being configured to manipulate data stored in the secondary data store but be limited to read-only access of data stored in the primary data store.

In the ambulatory medical device, the at least one processor may be configured to execute the at least one patient care component via a first processing thread and to execute the limited functionality component via a second processing thread. The memory in the ambulatory medical device may be configured to provide a primary data store and a secondary data store. The at least one processor may include a primary processor and a secondary processor. The at least one patient care component may be executable by the primary processor and may be configured to manipulate primary data stored in the primary data store and manipulate secondary data stored in the secondary data store. The limited functionality component may be executable by the secondary processor and may be configured to not affect the one or more primary operations of the ambulatory medical device at least in part by being configured to manipulate data stored in the secondary data store but be limited to read-only access of data stored in the primary data store.

In the ambulatory medical device, the limited functionality component may be configured to not affect the one or more primary operations of the ambulatory medical device at least in part by being configured to limit execution of one or more commands received from the communication device. The limited functionality component may be configured to limit execution of the one or more commands to those one or more commands that do not affect the one or more primary operations of the ambulatory medical device. The limited functionality component may be configured to either limit or shut down execution of the one or more commands based at least on one of a threshold number of commands per time period, a threshold number of commands based on a type of the at least one processor, a threshold number of active streams, a threshold percentage utilization of the at least one processor, a threshold percentage memory consumed, and a threshold number of threads.

The ambulatory medical device may further include a battery for providing battery power to the ambulatory medical device. The limited functionality component may be configured to either limit or shut down execution of the one or more commands upon detecting that an amount of battery power transgresses a threshold value. The limited functionality component may be configured to authenticate the information received from the communication device as originating from one or more previously identified communication devices. The limited functionality component may be configured to authenticate the information received from the communication device using at least one of password authentication and certificate-based authentication.

The ambulatory medical device may further include a user interface component. The limited functionality component may be configured to send one or more interface commands to the user interface component. The one or more interface commands may be configured to initiate output of one or more messages via the user interface component. The one or more messages may be predefined within the ambulatory medical device. The limited functionality component may be configured to execute an interface command configured to modify a message to be output by the user interface component and to send one or more interface commands to the user interface component, the one or more interface commands comprising at least one interface command configured to initiate output of the message. The interface command may be configured to not affect the one or more primary operations of the ambulatory medical device at least in part by being configured to determine whether the message can be modified based on identifying whether the message is flagged as restricted from modification. The limited functionality component may be configured to send one or more interface commands to the user interface component based on the one or more commands received from the communication device.

In the ambulatory medical device, the at least one sensor may include at least one of a tissue fluid sensor, a heart sounds sensor, a lung sounds sensor, an accelerometer, and a pulse oximeter. The limited functionality component may include an application program interface implemented using at least one of a representational state transfer, JavaScript object notation, extensible markup language, transmission control protocol socket, and encrypted uniform resource locator parameters. In the ambulatory medical device, the at least one command of the one or more commands may be further configured to initiate transmission of information from the ambulatory medical device to the communication device. The at least one command may be configured to initiate transmission of the information from the ambulatory medical device to the communication device (a) in response to a predetermined condition, (b) substantially in real time, (c) during an occurrence of the predetermined condition, (d) in response to user input, (e) in response to a predetermined triggering event, (f) continuously over a period of time, (g) substantially continuously over a period of time, (h) during periodic time intervals, or (i) during aperiodic time intervals. The information may be descriptive of at least one of the patient's cardiac function and a status of the ambulatory medical device. The information may include at least one of electrocardiogram data, heart sound data, patient location data, ambulatory medical device status data, patient name, electrode fall-off status, and compliance data. The ambulatory medical device may include a cardiac monitor configured to either continuous or substantially continuous monitor a patient via the at least one sensor and provide a treatment to the patient via one or more therapy electrodes. The ambulatory medical device may include a cardiac monitor configured to provide a treatment to the patient via one or more adhesive electrodes.

In another example, a communication device is provided. The communication device is configured to interoperate with a wearable defibrillator. The communication device includes a first wireless interface configured to communicate with the wearable defibrillator; a second wireless interface configured to communicate with a remote computer; and at least one processor coupled to the first wireless interface and the second wireless interface and configure to exclusively execute a hotspot component upon powering up, the hotspot component being configured to automatically establish a first secure connection to the wearable defibrillator via the first wireless interface, to receive cardiac information regarding a patient from the wearable defibrillator via the first connection, to automatically establish a second connection to the remote computer via the second wireless interface, and to transmit the cardiac information regarding the patient to the remote computer via the second connection, the cardiac information comprising at least one of physiological parameters of the patient and information regarding compliance by the patient to a prescribed treatment schedule. The communication device may be housed within the wearable medical device or a base station. The hotspot component may be configured to calculate a signal strength of the first connection and to transmit information regarding the signal strength to the remote computer via the second connection.

In another example, communication device is provided. The communication device includes a user interface; a medical device interface configured to communicate with a medical device; and at least one processor coupled to the user interface and the medical device interface and configure to transmit, via the medical device interface, at least one command to monitor a patient parameter; to receive, via the interface, one or more values of the patient parameter; to analyze the one or more values; and to display, via the user interface, information descriptive of the one or more values.

In the communication device, the patient parameter may include patient heart rate and the information descriptive of the one or more values may include a heart rate trend over a period to time. The communication device may further include a network interface configured to communicate with a remote computer. The at least one processor may be configured to transmit the one or more values to the remote computer via the network interface. The at least one processor may be configured to receive, from the remote computer via the network interface, a command to display an instruction to the patient and to display the instruction to the patient via the user interface.

In another example, a system is provided. The system includes a communication device in communication with an external sensor and an ambulatory medical device. The ambulatory medical device includes at least one sensor configured to acquire data descriptive of the patient; one or more processors in communication with the at least one sensor; a patient care component executable by the one or more processors and configured to perform one or more primary operations of the ambulatory medical device at least in part by accessing the data descriptive of the patient; and a limited functionality component executable by the one or more processors and configured to execute commands received from the communication device, the limited functionality component configured to not affect the one or more primary operations of the ambulatory medical device.

In the system, the communication device may include at least one of another medical device distinct from the ambulatory medical device, a wearable device distinct from the ambulatory medical device, a charger of the ambulatory medical device, a base station of the ambulatory medical device, and a smart phone, wherein the wearable device comprises at least one of a watch, anklet, necklace, belt buckle, and glasses. The ambulatory medical device may include a user interface component and the commands may include at least one command configured to receive information descriptive of the communication device and request that the user interface component display the information. The information may describe at least one of an image stored on the communication device, a signal strength of a network connection between the ambulatory medical device and the communication device, and an amount of power remaining in a battery comprised within the communication device. The communication device may be included within the ambulatory medical device.

In the system, the communication device may be further configured to generate a request to execute a command to configure a threshold value for a patient parameter monitored by the ambulatory medical device and to transmit the request to the limited functionality component. The limited functionality component may be further configured to receive the request; parse the request to identify the command and the threshold value; execute the command; monitor, in response to executing the command, the patient parameter to determine whether the patient parameter transgresses the threshold value; and transmit a notification to a recipient device where the patient parameter transgresses the threshold value. The patient parameter may include heart beats per minute (bpm) or time elapsed since the patient last complied with a prescribed treatment schedule. The threshold value may include of 180 bpm or a prescribed time interval within the prescribed treatment schedule. The prescribed treatment schedule may require at least one of a rehabilitation session and taking medication.

Still other aspects, examples and advantages of these aspects and examples, are discussed in detail below. Moreover, it is to be understood that both the foregoing information and the following detailed description are merely illustrative examples of various aspects and features, and are intended to provide an overview or framework for understanding the nature and character of the claimed aspects and examples. Any example or feature disclosed herein may be combined with any other example or feature. References to different examples are not necessarily mutually exclusive and are intended to indicate that a particular feature, structure, or characteristic described in connection with the example may be included in at least one example. The appearances of such terms herein are not necessarily all referring to the same example.

DESCRIPTION OF DRAWINGS

Various aspects of at least one example are discussed below with reference to the accompanying figures, which are not intended to be drawn to scale. The figures are included to provide an illustration and a further understanding of the various aspects and examples, and are incorporated in and constitute a part of this specification, but are not intended as a definition of the limits of any particular example. The drawings, together with the remainder of the specification, serve to explain principles and operations of the described and claimed aspects and examples. In the figures, each identical or nearly identical component that is illustrated in various figures is represented by a like numeral. For purposes of clarity, not every component may be labeled in every figure. In the drawings:

DETAILED DESCRIPTION

Figure 1:
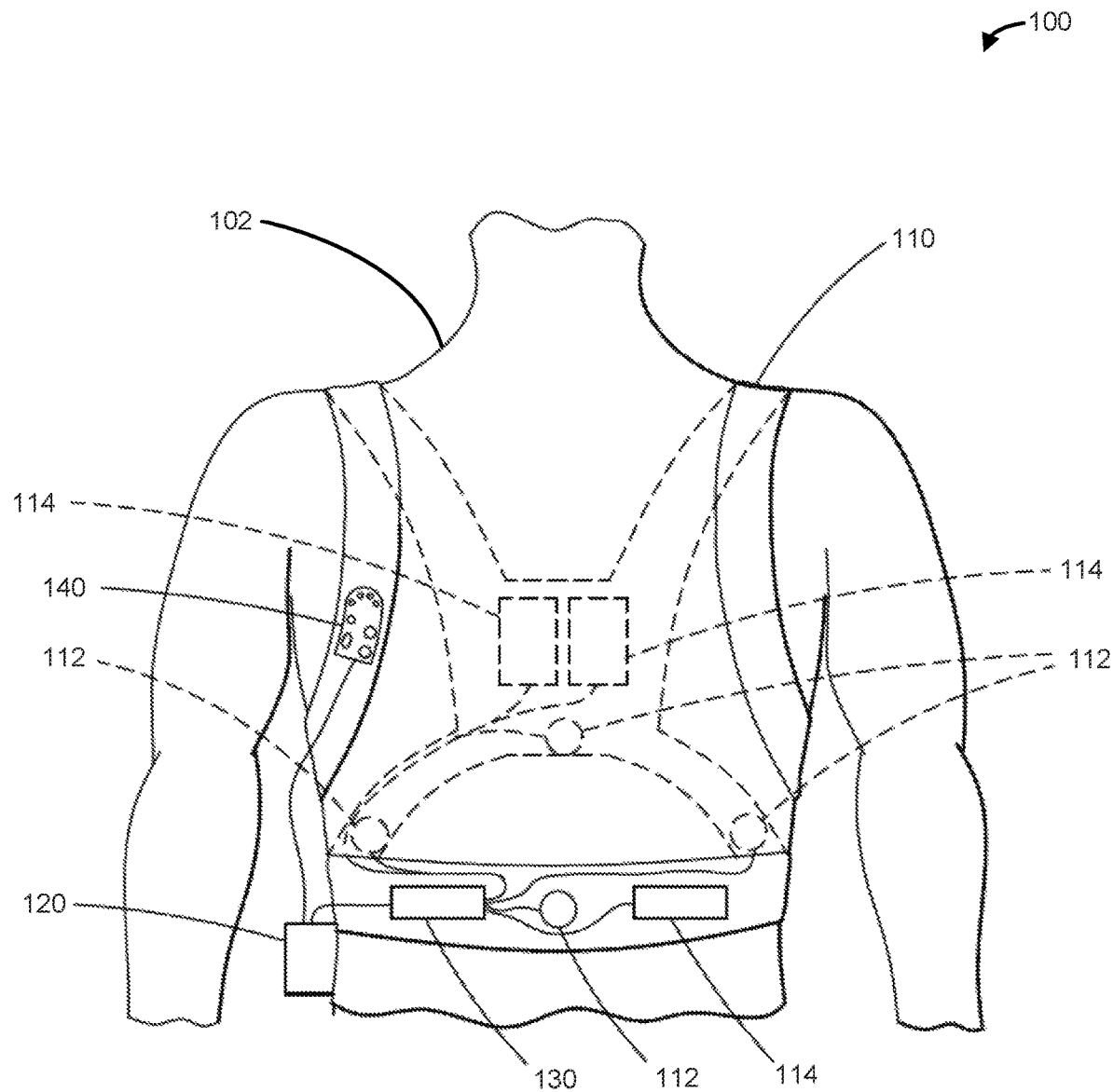
FIG. 1 is a schematic diagram of one example of a medical device.

Systems and techniques as disclosed herein can be configured to facilitate secure and limited interactions with medical devices. The medical devices as disclosed herein may monitor a person (e.g., a patient) and, in some implementations, provide treatment to the person based on the monitoring. For example, the medical device can monitor one or more physiological parameters of the person. For instance, the medical device can be configured to monitor data digitized from one or more physiological signals of a patient (e.g., electrocardiograph (ECG) data), heart beats, respiration, breath sounds, tissue fluids, lung fluids, lung sounds, chest movements, and/or cardiopulmonary anomalies and determine whether the detected anomalies impair cardiac or pulmonary function. In various implementations, the medical device can be configured to monitor other patient parameters including but not limited to blood pressure, glucose levels, weight, blood oxygen, etc.

For example, medical devices as disclosed herein can be configured to determine whether the patient may be experiencing a cardiac condition. The medical devices can include a plurality of sensing electrodes that are disposed at one or more locations of the patient's body and configured to sense or monitor the cardiac signals of the patient. In some implementations, the medical device can be configured to monitor, in addition to cardiac signals, heart sounds, lung sounds, respiration, chest movements, and/or other patient body movement information. For example, such devices can be used as cardiac monitors in certain cardiac monitoring applications, such as holter monitoring, mobile cardiac telemetry (MCT) and/or continuous event monitoring (CEM) applications.

In some implementations, a medical device as disclosed herein can be configured to determine an appropriate treatment for the patient based on the sensed patient signals (e.g., cardiac signals, heart sounds, lung sounds, or other sensed information) and cause one or more therapeutic shocks (e.g., defibrillating and/or pacing shocks) to be delivered to the body of the patient as described in further detail below. Accordingly, the medical device can include a plurality of therapy electrodes that are disposed at one or more locations of the patient's body and configured to deliver the therapeutic shocks.

A medical device as described herein can be configured to monitor a patient for a cardiac arrhythmia condition such as bradycardia, ventricular tachycardia (VT) or ventricular fibrillation (VF). In addition, while the detection methods and systems described hereinafter are disclosed as detecting VT and VF, this is not to be construed as limiting the examples disclosed herein as other arrhythmias, such as, but not limited to, atrial arrhythmias including premature atrial contractions (PACs), multifocal atrial tachycardia, atrial flutter, and atrial fibrillation, supraventricular tachycardia (SVT), junctional arrhythmias, tachycardia, junctional rhythm, junctional tachycardia, premature junctional contraction, and ventricular arrhythmias including premature ventricular contractions (PVCs) and accelerated idioventricular rhythm, may also be detected. In the case of treatment devices, such as, pacing and/or defibrillating devices, if an arrhythmia condition is detected, the device can automatically provide a pacing or defibrillation pulse or shock to treat the condition.

In some implementations, a medical device includes a limited functionality component that is configured to exchange (e.g., transmit or receive) information with a communication device in a manner that does not affect any primary operation of the medical device. For example, such a limited functionality component can be configured to be unable to affect any primary operation of the medical device. The medical device may be a cardiac monitor that includes a limited functionality component that transmits data descriptive of the cardiac function of a patient to a communication device in the form of a smart phone. In this example, the limited functionality component may monitor computing resources (e.g., compute or data storage resources) available for the primary operations of the medical device and adjust computing resources utilized by limited functionality operations to ensure the primary operations are not impacted. This adjustment may include restricting limited functionality operations to a threshold number of operations per time period, a threshold number of threads, specific thread priorities, specific types of data operations, specific data stores or a threshold utilization of specific data stores, specific actual or virtual processors or processor types, a threshold utilization of one or more actual or virtual processors, and the like. In some implementations, the limited functionality component may be configured to restrict or shut down its functionality in certain situations. Such situations include but are not limited to: when the component consumes resources (e.g., operations per time period, number of threads, data storage utilization, and the like) that transgresses a predetermined threshold, the battery power available in the medical device reaches a predetermined level, or when a critical operation of the device is ongoing (e.g., when a treatment protocol is being executed by the device).

In some implementations, the information exchanged between the limited functionality component and the communication device includes one or more commands that the limited functionality component is configured to execute and one or more responses resulting from command execution. For example, the limited functionality component may receive a command to stream cardiac data to the communication device and the communication device may process the stream in response to receipt of the command.

In some implementations, a primary operation of a medical device is any operation of the medical device that causes the medical device to be subject to government regulation as of the filing date of the present disclosure. For instance, a primary operation of a medical device may be any operation of the medical device that causes the medical device to be subject to Title 21 of the U.S. Code of Federal Regulations Chapter I, Subchapter H, such as Part 814 of the Regulations concerning pre-market approvals of medical devices, as of the filing date of the present disclosure. In other examples, a primary operation of a medical device includes any operation that affects patient safety and/or device efficacy with respect to the prescribed purpose of the medical device. In other examples, a primary operation of a medical device includes any operation critical to the prescribed purpose of the medical device. Thus the primary operation or operations of medical devices vary with the designs of the medical devices and the jurisdictions within which the medical devices operate. Examples of critical operations include monitoring a patient for a predetermined patient condition, providing information relating to the predetermined patient condition to a person, receiving user input relating to the predetermined patient condition from the person, determining a therapy for the patient on detecting the predetermined patient condition, and providing the therapy to the patient based on the predetermined patient condition. Accordingly in such examples, the primary operations are executed by one or more patient care components of a medical device.

In some implementations, as noted above, primary operations can include device functions and operations that have the potential to affect the safety and efficacy of the medical device. In an implementation, such operations may relate to ensuring the integrity of one or more critical components of the medical device, e.g., all or some of the one or more patient care components. Such primary operations can include self-tests performed by the device, e.g., to verify the operational integrity of critical components of the medical device. For instance, in a cardiac treatment device such as a defibrillator, primary operations can include tests of the energy storage elements and associated circuitry. A defibrillator may periodically or aperiodically enable a high voltage converter circuit to charge one or more capacitor banks and take certain measurements to verify that the capacitor banks are able to properly charge up to the required levels.

In some implementations, for increased security, the limited functionality component can be configured to authenticate the communication device and determine whether the communication device is authorized to exchange information with the medical device. For example, the limited functionality component may process logon credentials prior to executing any commands requested by the communication device.

In some implementations, the limited functionality component initiates display of information received from the communication device on a display of the medical device. For example, the limited functionality component may initiate display of a physician's instructions on a touchscreen housed in the medical device. In some cases, the limited functionality component may initiate display of the remaining battery life of the communication device (e.g., a smart phone) on a touchscreen housed in the medical device.

Examples of the methods and systems discussed herein are not limited in application to the details of construction and the arrangement of components set forth in the following description or illustrated in the accompanying drawings. The methods and systems are capable of implementation in other examples and of being practiced or of being carried out in various ways. Examples of specific implementations are provided herein for illustrative purposes only and are not intended to be limiting. In particular, acts, components, elements and features discussed in connection with any one or more examples are not intended to be excluded from a similar role in any other examples.

Also, the phraseology and terminology used herein is for the purpose of description and should not be regarded as limiting. Any references to examples, components, elements or acts of the systems and methods herein referred to in the singular may also embrace examples including a plurality, and any references in plural to any example, component, element or act herein may also embrace examples including only a singularity. References in the singular or plural form are not intended to limit the presently disclosed systems or methods, their components, acts, or elements. The use herein of "including," "comprising," "having," "containing," "involving," and variations thereof is meant to encompass the items listed thereafter and equivalents thereof as well as additional items. References to "or" may be construed as inclusive so that any terms described using "or" may indicate any of a single, more than one, and all of the described terms. In addition, in the event of inconsistent usages of terms between this document and documents incorporated herein by reference, the term usage in the incorporated references is supplementary to that of this document; for irreconcilable inconsistencies, the term usage in this document controls.

Example Medical Devices

In some implementations, the systems, components, and/or techniques described herein can be used in a wide range of medical devices. For instance, such medical device can be internal (e.g., implantable), invasive, or external medical devices. For example, external medical devices may be in contrasted with internal devices, such as implantable medical devices. For example, the medical device can be a cardiac monitoring and/or pacing device or defibrillator, such as an in-facility continuous monitoring defibrillator (e.g., for patients that are confined to a limited space within a facility, such as, within a hospital environment, to a patient's room) or outpatient wearable defibrillators. The primary operations of these devices include monitoring patient cardiac function and, in some cases, treating cardiac arrhythmias, such as VT or VF. In at least some of these devices, the patient care components include monitoring, detecting, and treating components, such as the cardiac event detector 326, the sensor interface 312, and the therapy delivery interface 302.

In some implementations, an external medical device can be an automated cardiac monitor or defibrillator that can be used in certain specialized conditions and/or environments such as in combat zones or within emergency vehicles. The medical device can be configured so that it can be used immediately (or substantially immediately) in a life-saving emergency. For example, the external medical device can be an automated external defibrillator (AED) Such AEDs are available from ZOLL® Medical Corporation of Chelmsford, Mass.

In some implementations, the external medical device is an ambulatory device (e.g., a device that is capable of and designed for moving with the patient as the patient goes about his or her daily routine). In some examples, the external medical device can be configured as a wearable defibrillator, such as the LifeVest® wearable defibrillator available from ZOLL® Medical Corporation of Chelmsford, Mass.

The devices as described herein may be capable of continuously, substantially continuously, long-term and/or extended use or wear by, or attachment or connection to a patient.

For example, devices as described herein may be capable of being used or worn by, or attached or connected to a patient, without substantial interruption for a predetermined period of time. In some examples, such devices may be capable of being used or worn by, or attached or connected to a patient for example, up to hours or beyond (e.g., weeks, months, or even years).

In some implementations, such devices may be removed for a period of time before use, wear, attachment, or connection to the patient is resumed, e.g., to change batteries, to change the garment, and/or to take a shower, without departing from the scope of the examples described herein.

The devices as described herein may be capable of continuously, substantially continuously, long-term and/or extended monitoring of a patient.

For example, devices as described herein may be capable of providing cardiac monitoring without substantial interruption for a predetermined period of time. In some examples, such devices may be capable of continuously or substantially continuously monitoring a patient for cardiac-related information (e.g., ECG information, including arrhythmia information, heart sounds, etc.) and/or non-cardiac information (e.g., blood oxygen, the patient's temperature, glucose levels, and/or lung sounds), for example, up to hours or beyond (e.g., weeks, months, or even years).

In some implementations, such devices may be powered down for a period of time before monitoring is resumed, e.g., to change batteries, to change the garment, and/or to take a shower, without departing from the scope of the examples described herein.

In some instances, the devices may carry out monitoring in periodic or aperiodic time intervals or times. For example, the monitoring during intervals or times can be triggered by a user action or another event. For example, one or more durations between the periodic or aperiodic intervals or times can be user-configurable.

In various implementations, the devices may be operated on battery power for a duration of the device's use after which the batteries may be replaced and/or recharged.

In some implementations, the medical device as described herein can be a hospital-based wearable defibrillator and/or pacing device. For example, such a hospital-based device can include a defibrillator and/or pacing device configured for continuous or substantially continuous use, wear, connection, attachment, or monitoring to/of a patient in a hospital environment. The hospital-based device can include a plurality of therapy and sensing electrodes that are attached to the patient's skin. In some examples, the electrodes are disposable adhesive electrodes. In some implementations, the electrodes are affixed to an electrode assembly (a patch), which can then be adhesively attached to the patient's skin. The electrodes can be attached to the patient's skin at particular locations as prescribed by a trained professional.

In operation, the hospital-based device can include a monitor configured to operate in a manner that is different from that of the monitor of wearable defibrillator 100 described with respect to FIG. 1. As described in more detail herein, an interface, prompts, and communication performed by the hospital-based device can be configured for and/or directed to a user other than a patient, e.g., a caregiver such as a nurse or a patient service representative. For example, a caregiver can program the device and/or set the device up for use by the patient. The interface, prompts, and communication can be directed to the patient in scenarios such as when a response is required for the device to detect whether or not the patient is conscious, which can be used in deciding when to shock the patient, and when a patient is given an alert to call the caregiver.

In some implementations, the medical device as described herein can configured to perform a primary operation of monitoring a patient presenting with syncope (e.g., by analyzing the patient's cardiac activity for aberrant patterns that can indicate abnormal physiological function). In some examples, aberrant patterns may occur prior to, during, or after the onset of syncope symptoms. For example, the short-term outpatient defibrillator can include a plurality of electrodes and/or an electrode assembly (patch) that can be adhesively attached to the patient's skin. The patient may replace the electrodes and/or patches as prescribed.

For example, the medical device can include a user interface for interacting with the medical device. The device can include one or more input mechanisms (e.g., buttons) that the patient can interact with in order to respond to an alert (e.g., a treatment alert or a status alert). In some examples, the medical device issues a treatment alert before providing a treatment shock, and if the patient does not respond to the treatment alert (e.g., by holding down one or more response buttons), the device can deliver the treatment shock to restore normal heart rhythm. In some examples, the medical device issues a status alert where the device detects that an electrode (e.g. a sensing electrode) is not properly positioned on the patient's body. This type of status alert may be referred to herein as a "fall-off" status alert.

Example Wearable Medical Device

FIG. 1 illustrates an example medical device 100 that is wearable by the patient 102. The wearable medical device 100 includes a plurality of sensing electrodes 112 that can be disposed at various positions about the patient's body. The sensing electrodes 112 are electrically coupled (coupling not shown in the figure) to a medical device controller 120 through a connection pod 130. In some implementations, some of the components of the wearable medical device 100 are affixed to a garment 110 that can be worn on the patient's torso. For example, as shown in FIG. 1, the controller 120 can be mounted on a belt worn by the patient. The sensing electrodes 112 and connection pod 130 can be assembled or integrated into the garment 110 as shown. The sensing electrodes 112 are configured to monitor the cardiac function of the patient (e.g., by monitoring one or more cardiac signals of the patient). While FIG. 1 shows three sensing electrodes 112, additional sensing electrodes may be provided, and the plurality of sensing electrodes 112 may be disposed at various locations about the patient's body.

The wearable medical device 100 can also optionally include a plurality of therapy electrodes 114 that are electrically coupled (coupling not shown in the figure) to the medical device controller 120 through the connection pod 130. The therapy electrodes 114 are configured to deliver one or more therapeutic defibrillating shocks to the body of the patient if it is determined that such treatment is warranted. The connection pod 130 may include electronic circuitry and one or more sensors (e.g., a motion sensor, an accelerometer, etc.) that are configured to monitor patient activity. In some implementations, the wearable medical device 100 may be a monitoring only device that omits the therapy delivery capabilities and associated components (e.g., the therapy electrodes 114). In some implementations, various treatment components may be packaged into various components that can be attached or removed from the wearable medical device 100 as needed.

The controller 120 includes response buttons and a touch screen that the patient can interact with in order to communicate with the medical device 100. The controller 120 also includes a speaker for communicating information to the patient and/or a bystander. In some examples, when the controller 120 determines that the patient is experiencing cardiac arrhythmia, the speaker can issue an audible alarm to alert the patient and bystanders to the patient's medical condition. In some examples, the controller 120 can instruct the patient to press and hold one or both of the response buttons on the medical device controller 120 to indicate that the patient is conscious, thereby instructing the medical device controller 120 to withhold the delivery of one or more therapeutic defibrillating shocks. If the patient does not respond to an instruction from the controller 120, the medical device 100 may determine that the patient is unconscious and proceed with the treatment sequence, culminating in the delivery of one or more defibrillating shocks to the body of the patient.

Figure 2A:
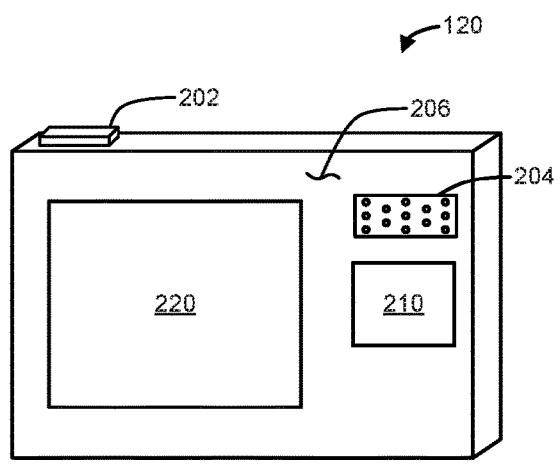
FIGS. 2A and 2B are schematic diagrams of a first side and a second side of one example of a medical device controller.
Figure 2B:
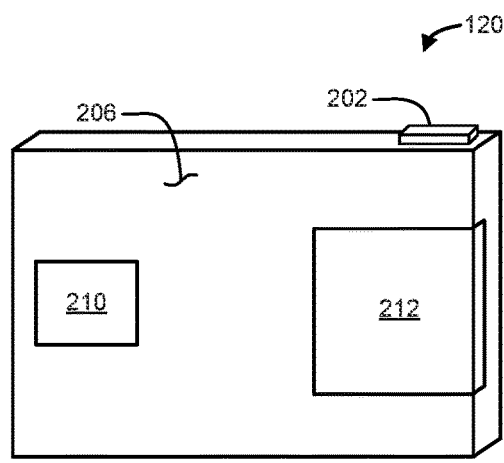

FIGS. 2A and 2B illustrate an example of the medical device controller 120. The controller 120 may be powered by a rechargeable battery 212. The rechargeable battery 212 may be removable from a housing 206 of the medical device controller 120 to enable a patient and/or caregiver to swap a depleted (or near depleted) battery 212 for a charged battery. The controller 120 includes a user interface such as a touch screen 220 that can provide information to the patient, caregiver, and/or bystanders. The patient and/or caregiver can interact with the touch screen 220 to control the medical device 100. The controller 120 also includes a speaker 204 for communicating information to the patient, caregiver, and/or the bystander. The controller 120 includes one or more response buttons 210. In some examples, when the controller 120 determines that the patient is experiencing cardiac arrhythmia, the speaker 204 can issue an audible alarm to alert the patient and bystanders to the patient's medical condition. In some examples, the controller 120 can instruct the patient to press and hold one or both of the response buttons 210 to indicate that the patient is conscious, thereby instructing the medical device controller 120 to withhold the delivery of therapeutic defibrillating shocks. If the patient does not respond to an instruction from the controller 120, the medical device 100 may determine that the patient is unconscious and proceed with the treatment sequence, culminating in the delivery of one or more defibrillating shocks to the body of the patient. The medical device controller 120 may further include a port 202 to removably connect sensing devices (e.g., ECG sensing electrodes 112) and/or therapeutic devices (e.g., therapy electrodes 114) to the medical device controller 120.

Figure 3:
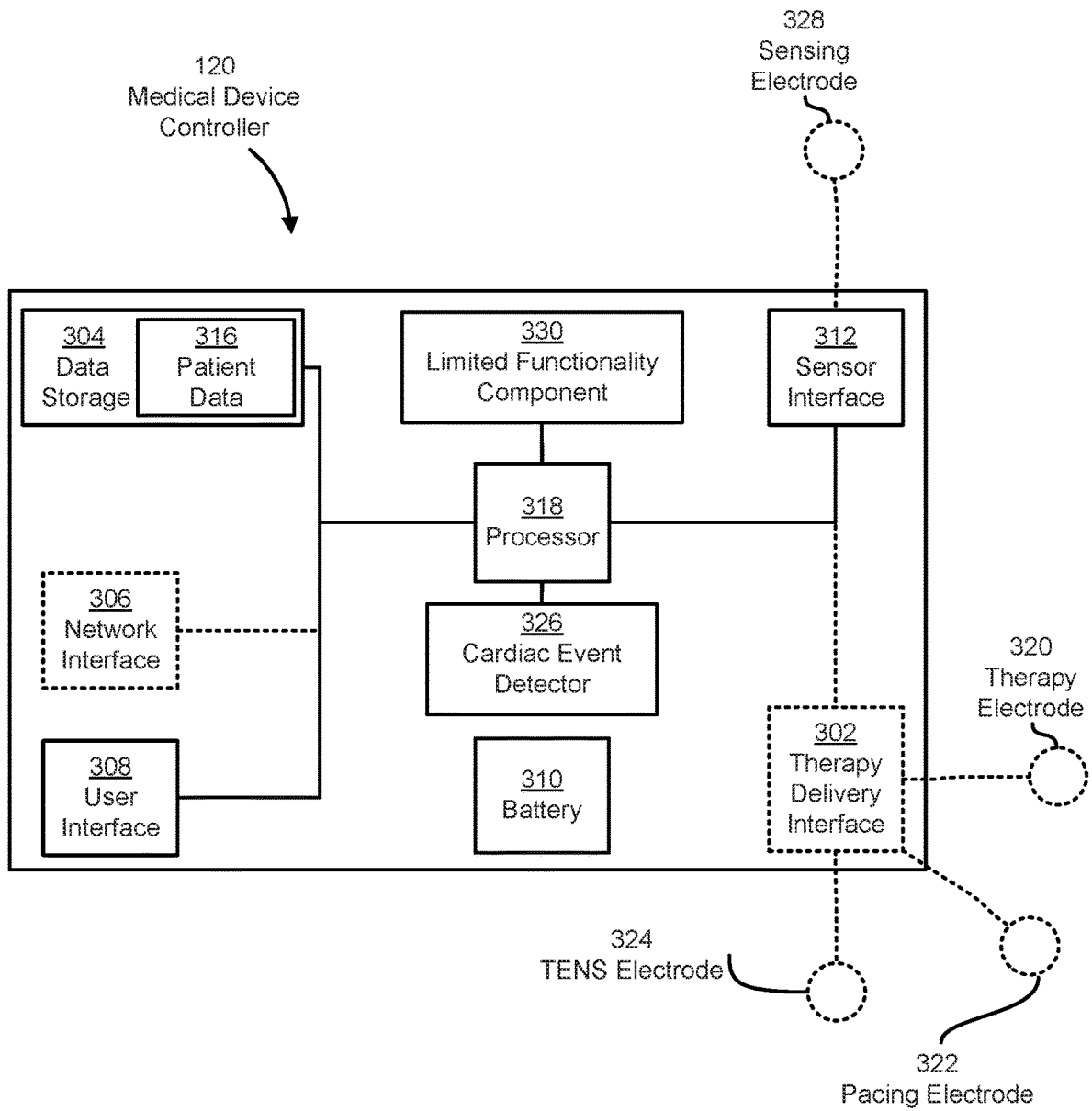
FIG. 3 is a block diagram of the example of the medical device controller illustrated in FIGS. 2A and 2B.

FIG. 3 shows a schematic of an example of the medical device controller 120 of FIGS. 1, 2A, and 2B. The controller 120 includes at least one processor 318, a limited functionality component 330, a sensor interface 312, an optional therapy delivery interface 302, data storage 304 (which may include patient data storage 316), an optional network interface 306, a user interface 308 (e.g., including the touch screen 220 shown in FIG. 2), and a battery 310. The sensor interface 312 may be coupled to any one or combination of sensors to receive information indicative of patient parameters. For example, the sensor interface 312 may be coupled to one or more sensing devices including, for example, sensing electrodes 328. The therapy delivery interface 302 (if included) may be coupled to one or more electrodes that provide therapy to the patient including, for example, one or more therapy electrodes 320, pacing electrodes 322, and/or TENS electrodes 324. The sensor interface 312 and the therapy delivery interface 302 may implement a variety of coupling and communication techniques for facilitating the exchange of data between the sensors and/or therapy delivery devices and the controller 120.

In some examples, the network interface 306 can facilitate the communication of information between the controller 120 and one or more other devices or entities over a communications network. For example, the network interface 306 may be configured to communicate with a server (e.g., a remote server) where a caregiver can access information related to the patient. As discussed in more detail below with reference to FIG. 4, the network interface 306 may facilitate communication between the medical device controller 120 and a base station associated (e.g., paired) with the medical device controller.

In some examples, the medical device controller includes a cardiac event detector 326 to monitor the cardiac activity of the patient and identify cardiac events experienced by the patient based on received cardiac signals. The cardiac event detector 326 may be configured to execute one or more heartbeat detection processes and/or arrhythmia detection processes. In some examples, the cardiac event detector 326 can access patient templates (e.g., which may be stored in the data storage 304 as patient data 316) that can assist the cardiac event detector 326 in identifying cardiac events experienced by the particular patient.

In some implementations, the processor 318 includes one or more processors that each can perform a series of instructions that result in manipulated data and/or control the operation of the other components of the controller 120. In some examples, the limited functionality component 330 is implemented as a software component that is stored in the data storage 304 and executed by the at least one processor 318 to expose, for example, a limited functionality interface to one or more communication devices (e.g., the communication devices described below with reference to FIGS. 10 and 11).

In some examples, the limited functionality component 330 is configured to implement a limited functionality interface through which the controller 120 receives, processes, and responds to commands defined within a limited functionality command set. Some additional examples of the controller 120 configured to execute the limited functionality component 330 in isolation from other components are described further below with reference to FIG. 7. Some examples of processes executed by the limited functionality component 330 are described further below with reference to FIGS. 8 and 9.

The controller 120 may be well-suited for a range of different cardiac monitoring and/or treatment devices and some additional examples of medical devices that incorporate the controller 120 are described further below.

In various implementations, the controller 120 comprises an embedded Linux operating system that supplies file system and networking support. In one example, the controller 120 includes software features that provide relational database functionality, touch screen display drivers, audio generation, BLUETOOTH wireless networking, networking security and firewalling, and a lightweight web server (as may be included in or controlled by the limited functionality component 330) and data encryption services. The controller 120 can implement a data security model to prevent unauthorized access to the controller 120 and access only by authorized authenticated communication devices and/or servers. Accordingly, for any wireless transmission (e.g., BLUETOOTH, WI-FI, or others) between the controller 120 and the communication device, multiple layers of security can be deployed. For instance, firewall rules may be implemented in the one or more operating systems of the controller 120 (including components executing under separate and distinct operating systems such as the limited functionality component 330) and the operating system of the communication device that will not permit external connections if they do not originate for an authorized and authenticated device. For example, connections to the communication device may be only made through an authorized remote server (as described in FIGS. 10-12 below). In addition to the firewall rules above, each controller 120 may require a unique secure login key. In some implementations, communications between one or more of the controller 120 and the communication device and the communication device and the remote server may be configured to be via a Virtual Private Network (VPN). Further, the controller 120 (e.g., the limited functionality component 330 in the controller 120) can be configured to encrypt any data transmitted to the communication device and/or the remote server in compliance with prescribed security mechanisms for patient data. For example, such an encryption standard may be an AES 256 bit Cypher Block Chaining Technology.

Example Base Station

Figure 4:
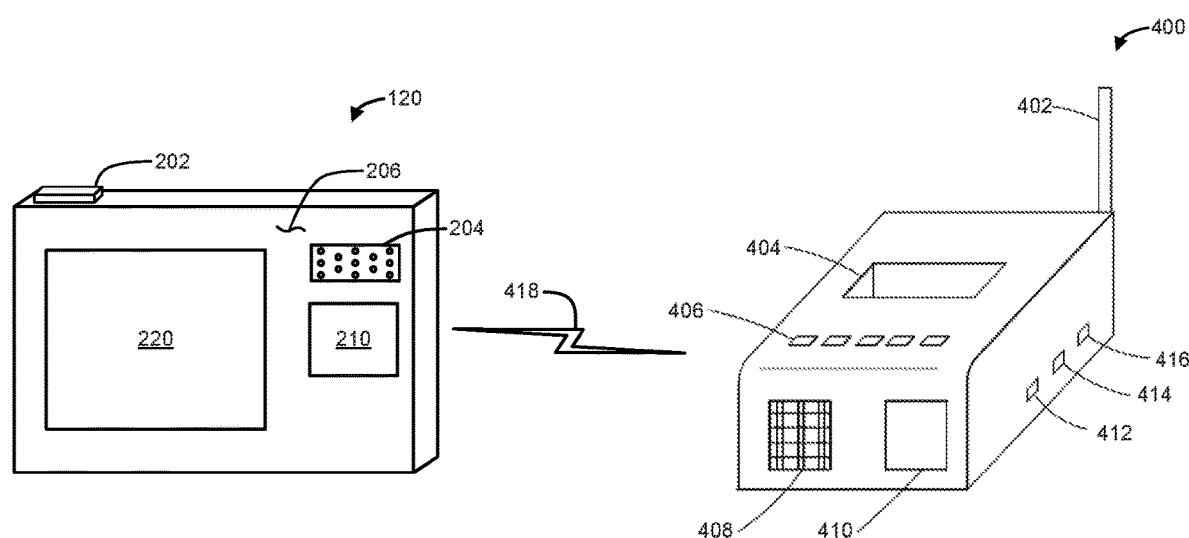
FIG. 4 is a schematic diagram of an example system including a medical device and a base station.

In some examples, the medical device controller may be in communication with a base station capable of performing a number of different functions. FIG. 4 illustrates an example medical device controller 120 in communication with a base station 400. As illustrated, base station 400 includes an antenna 402, a battery charging bay 404, one or more buttons 406, a speaker 408, a display 410, and one or more communication interfaces 412, 414, and 416. It is appreciated that the base station 400, in some examples, may omit one or more of the elements depicted in FIG. 4.

The base station 400 communicates with the medical device controller via, for example, wireless communication connection 418. The wireless communication connection may be implemented through any one or combination of wireless communication standards and protocols including, for example, BLUETOOTH, Wireless USB, ZigBee, and Wireless Ethernet. In some examples, the medical device controller 120 may be paired to a particular base station 400 through one or more procedures as described further below. The medical device controller 120 may provide, for example, information regarding the patient's medical condition and/or the status of the medical device to the base station 400.

The information received by the base station 400 may be communicated over a network shortly after it is received by the base station 400, or alternatively, may be stored in a memory of the base station 400 and communicated over the network at a later time. The information that is communicated by the base station 400 may be retained in the memory of the base station 400.

Another of the functions performed by the base station 400 is to store and/or communicate information received from the medical device controller 120 over a wired or wireless communication network. For example, information relating to the patient's medical condition over a period of time may be communicated by the base station 400 to a medical service provider, such as a doctor, so that the doctor may remotely monitor the patient's medical condition. The base station 400 also includes several different communication interfaces. These communication interfaces include a device communication interface 412 to receive information from the controller 120 of the medical device controller 120, a telephone network interface 414 to communicate, via a telephone network, the information received from the medical device controller 120, and a network interface 416 to communicate, via a wired network connection, the information received from the medical device controller 120. In certain embodiments, the base station 400 also includes an antenna 402 that can wirelessly communicate the information received from the medical device controller 120 via a cellular (e.g., 2G, 3G, and 4G) network.

In some examples, the base station 400 is capable of charging a rechargeable battery for the medical device controller 120. In these examples, the base station 400 may include a battery charging bay 404 constructed to receive and charge a battery for the medical device controller (e.g., battery 212). The medical device may be provided with multiple batteries to enable a patient and/or caregiver to charge one battery while another charged battery is used to provide power to the medical device. The batteries may be swapped between the medical device controller 120 and the base station 400 once the battery in the medical device controller is depleted (or near depleted). It is appreciated that the base station 400 may include any number of battery charging bays 404 to, for example, charge multiple batteries for the medical device controller 120 simultaneously.

In some examples, the base station 400 is constructed to house a communication device, such as the communication devices described further below with reference to FIGS. 10 and 11. For example, the communication device can be incorporated in an enclosure in the base station 400 and to prevent removal of the communication device in the field by persons other than authorized personnel.

In some implementations, the communication device may be releasably secured and/or coupled into a receptacle of the base station. For instance, where the communication device is implemented as or incorporated into a smart phone and/or other portable programmable device, the patient may remove the device and carry it elsewhere, e.g., on his/her person.

Example Hospital Based Medical Device

As discussed above, the medical device controller 120 may be well-suited for a range of different cardiac monitoring and/or treatment devices. In some examples, the medical device controller 120 is part of a hospital based medical device. In operation, the hospital based medical device may operate in a manner that is different from that of the wearable medical device 100 described above with respect to FIG. 1. As described in more detail herein, an interface, prompts, and communications performed by the hospital based medical device can be configured for and/or directed to a user other than the patient 102, e.g., a caregiver such as a nurse or a patient service representative. For example, a caregiver can program the medical device and/or set the medical device up for use by the patient 102. The interface, prompts, and communications can be directed to the patient 102 in scenarios such as when a response is required to enable the medical device to detect whether or not the patient 102 is conscious, which can be referenced in determining when to shock the patient 102, and when a patient is given an alert to call the caregiver.

Figure 5:
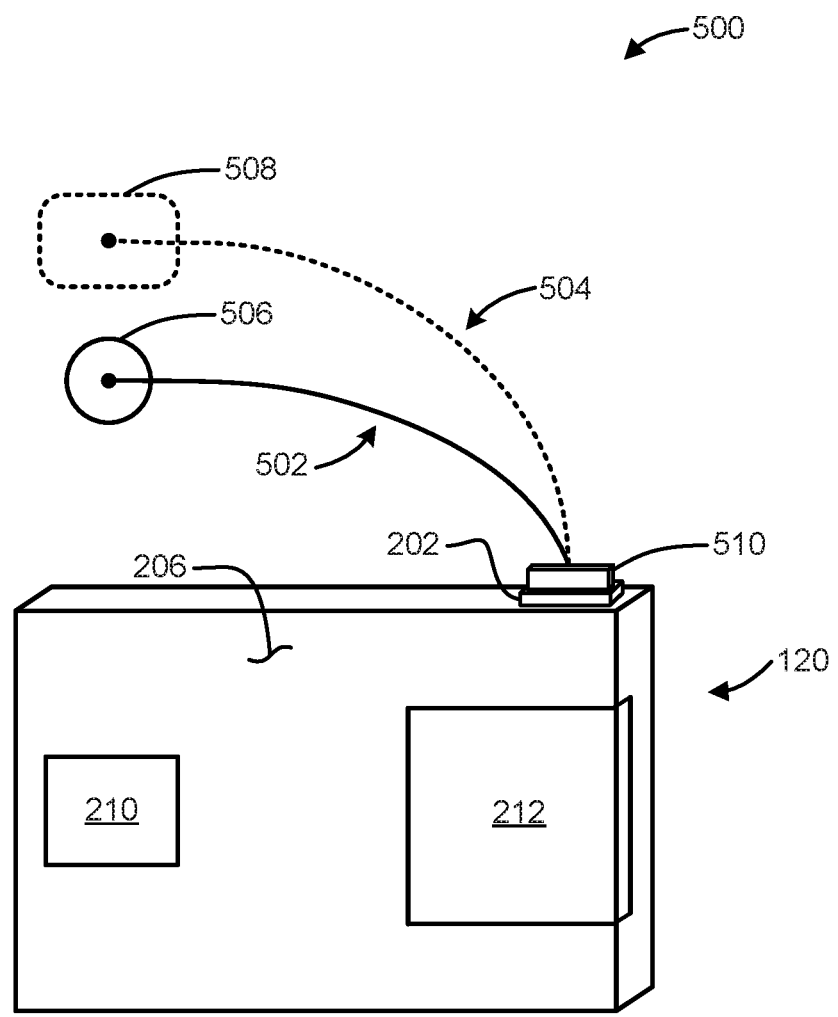
FIG. 5 is a schematic diagram of another example of a medical device.

FIG. 5 illustrates an example hospital based medical device employing the medical device controller 120. The hospital based medical device may be constructed to provide cardiac monitoring and/or treatment for patients in a hospital setting who may be, for example, bedridden patients. Providing patients in a hospital with the hospital based medical device may advantageously reduce the time between the patient experiencing a cardiac event and the notification of hospital staff, the administration of life-saving defibrillation pulses, and/or the administration of pacing pulses. Without the hospital based medical device, hospital patients may experience a cardiac event and have to wait for a physician to go to the patient's room, assess the condition of the patient, locate a defibrillation device, attach the defibrillation device to the patient, and provide treatment to the patient. Reducing the time between the patient experiencing a life-threatening cardiac event and providing life-saving defibrillation pulses can improve the likelihood of the patient surviving the cardiac event.

As illustrated in FIG. 5, the hospital based medical device 500 includes the medical device controller 120 and a sensing component 502. The sensing component 502 includes a connector 510 constructed to removably couple to the port 202 of the medical device controller 120. The sensing component 502 may sense information indicative of cardiac activity of the patient including, for example, ECG activity, tissue fluid, lung fluid, lung sounds, heart sounds, and/or patient activity. In some examples, the sensing component 502 includes one or more electrodes 506. The electrodes 506 may be stick-on adhesive electrodes constructed to attach to the patient. In some examples, the electrodes 506 may be detachable from a wire lead coupling the electrode 506 to the connector 510. Constructing the sensing component 502 to make the electrodes 506 detachable may enable the patient and/or caregiver to periodically (e.g., every 24 hours) replace the electrodes 506 without replacing the entire sensing component 502. The electrodes 506 may be long term wear electrodes that are configured to be continuously worn by a patient for extended periods (e.g., 3 or more days). One example of such a long term wear electrode is described in U.S. Patent Application Publication No. US2013/0325096, titled "LONG TERM WEAR MULTIFUNCTION BIOMEDICAL ELECTRODE," published Dec. 5, 2013 (hereinafter the "'096 publication"), which is attached hereto as Appendix A and which is hereby incorporated herein by reference in its entirety.

In some examples, the hospital based medical device 500 may also include a treatment component 504 to provide treatment to the patient. The treatment component 504 may include, for example, a therapy pad 508 configured to attach to the patient. The treatment component 504 may be connected to the same connector 510 as the sensing component 502 and/or employ a separate connector that is capable of coupling to the connector 510 in a modular fashion. It is appreciated that the treatment component 504 may be integrated into the sensing component 502 in a combined sensing treatment component. The combined sensing treatment component may include an electrode with integrated sensing and treatment delivery capabilities as described in the '096 publication.

In some examples, the controller 120 of the hospital based medical device 500 is communicatively coupled to a base station such as base station 400 described above. The hospital based medical device 500 may communicate, for example, patient information and/or status information of the medical device to the base station 400. In these examples, the base station 400 may issue alerts to medical personnel (e.g., at the hospital) and/or provide the information to a remote server that is accessible by medical personnel.

Example Monitoring Medical Device

In some examples, the medical device may be a patient monitoring device. For example, such a patient monitoring device may be configured to monitor one or more of a patient's physiological parameters without an accompanying treatment component. For example, a patient monitor may include a cardiac monitor for monitoring a patient's cardiac information. Such cardiac information can include, without limitation, heart rate, ECG data, heart sounds data from an acoustic sensor, and other cardiac or pulmonary data. In addition to cardiac monitoring, the patient monitor may perform monitoring of other relevant patient parameters, including glucose levels, blood oxygen levels, lung fluids, lung sounds, and blood pressure using various sensors, such as tissue fluid sensors, heart sounds sensors, lung sound sensors, and pulse oximetry sensors. The primary operations of the patient monitor include monitoring these patient parameters.

Figure 6:
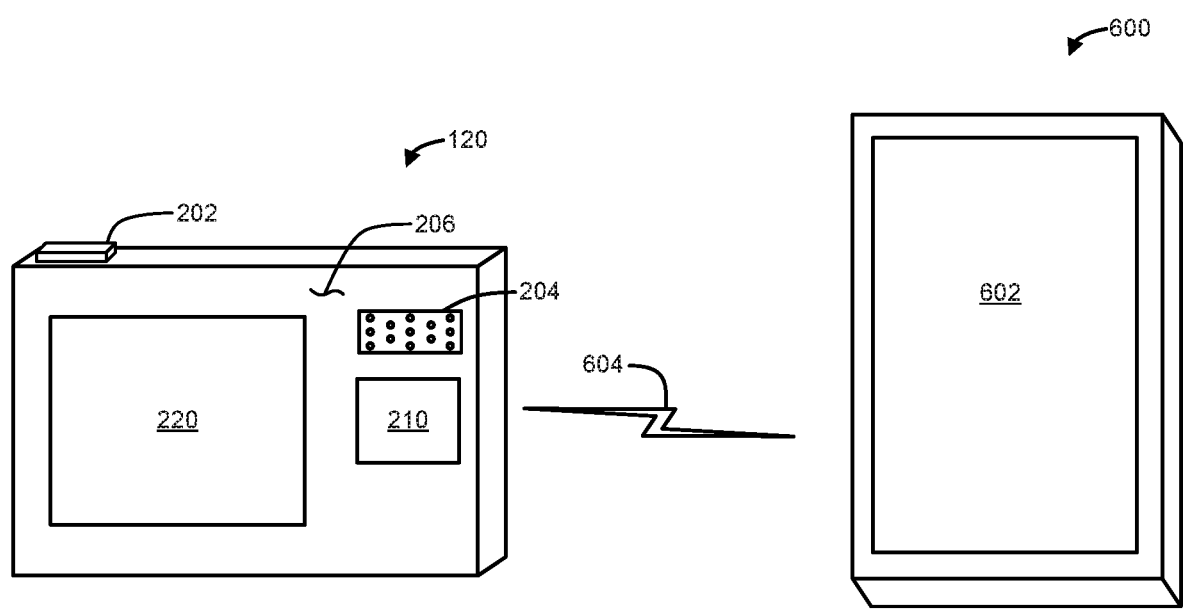
FIG. 6 is a schematic diagram of another example of a medical device.

FIG. 6 illustrates an example cardiac monitoring medical device, e.g., a cardiac monitor 600. In some implementations, the cardiac monitor 600 is capable of and designed for being worn by a patient who is at risk of developing cardiac problems, but who does not yet meet criteria to be outfitted with a medical device that includes a treatment component (e.g., a defibrillator). Thus, the cardiac monitor 600 may be prescribed so that continuous and/or event-based data can be sent from the cardiac monitor 600 to a server (e.g., a remote server). A caregiver can access the data from the remote server and determine whether the patient is experiencing or has experienced a cardiac problem. In some implementations, after determining that the patient is experiencing a cardiac problem, the caregiver may instruct the patient to begin wearing a medical device with treatment capabilities.

The cardiac monitor 600 includes the medical device controller 120 of FIGS. 1-3 along with associated components. In an implementation, the controller 120 operates in a similar fashion as described above. The cardiac monitor includes the plurality of sensing electrodes 112. In some examples, the sensing electrodes 112 can be an integral part of a housing structure of the cardiac monitor 600. In other examples, the cardiac monitor 600 includes a discrete housing structure that is distinct from a housing structure of the controller 120. In these examples, the cardiac monitor 600 communicates with the controller 120 via a wired or wireless network connection, such as the wireless connection 604. The network connection may be implemented through any one or combination of wireless communication standards and protocols including, for example, BLUETOOTH, Wireless USB, ZigBee, and Wireless Ethernet.

In some implementations, the patient can interact with the user interface 602 to identify a patient symptom. The user interface 602 may include a touchscreen that provides a drop down menu or check list which, in turn, allows the patient to select a particular symptom from a list of alternatives. Options for patient systems can include one or more of: feeling a skipped beat, shortness of breath, light headedness, racing heart rate, fatigue, fainting, chest discomfort, weakness, dizziness, and/or giddiness. In addition, the patient can select a level of activity (e.g., light activity, moderate activity, rigorous activity, etc.) that he or she was performing when the symptom occurred. In some implementations, in response to the selection by the patient, the cardiac event detector 326 can cause a portion of patient physiological information (e.g., in the form of a cardiac signal) to be captured for a length of time that is based on when the symptom was experienced. For example, the cardiac event detector 326 can cause a portion of an ECG signal of the patient to be captured. The portion of the ECG signal is sometimes referred to herein as an ECG strip. In some implementations, the cardiac monitor 600 can continuously record ECG data, and at the same time also identify and record one or more ECG strips relating to one or more events of interest (e.g., patient-reported symptoms, events detected by the cardiac event detector 326, etc.). As such, if a caregiver wishes to view ECG data for a period of time prior to or after the recorded ECG strip relating to an event of interest, such data is available for review from the continuously-recorded ECG data.

Limited Functionality Component

As described above, in some examples, a medical device includes a limited functionality component (e.g., the limited functionality component 330) that is configured to implement a limited functionality interface through which a medical device controller (e.g., the controller 120) receives, processes, and responds to commands defined within a limited functionality command set. This interface may be an application program interface (API) that is implemented using a variety of interoperability standards and architectural styles. For instance, in one example, the interface is a web services interface implemented using a representational state transfer (REST) architectural style. In this example, the interface communicates with a communication device (e.g., the communication devices described below with reference to FIGS. 10 and 11) using Hypertext Transfer Protocol (HTTP) along with JavaScript Object Notation and/or extensible markup language. In some examples, portions of the HTTP communications may be encrypted to increase security, such as by use of HTTPS and/or encrypted URI arguments. In other examples, the API is implemented using a proprietary application protocol accessible via a transmission control protocol socket. Thus the limited functionality interface as described herein is not limited to a particular implementation standard.

Both the contents of the command set and the manner in which the command set is executed by the limited functionality component are configured to not affect any primary operation of the medical device. In some examples, such contents and manner in which the command set is executed by the limited functionality component are configured to be unable to affect any primary operation of the medical device. For instance, the medical device and the limited functionality component are configured so that the command set is executed using secondary computing resources that are isolated from primary computing resources used to execute primary operations. This isolation may be physical isolation (e.g., different physical processors or different physical processing cores) or virtual (e.g., different virtual processors, different processing threads having the same or different thread priorities). By isolating resources used to execute primary operations from resources used to execute limited functionality operations, these examples render the limited functionality component unable to affect the primary operations.

Figure 7:
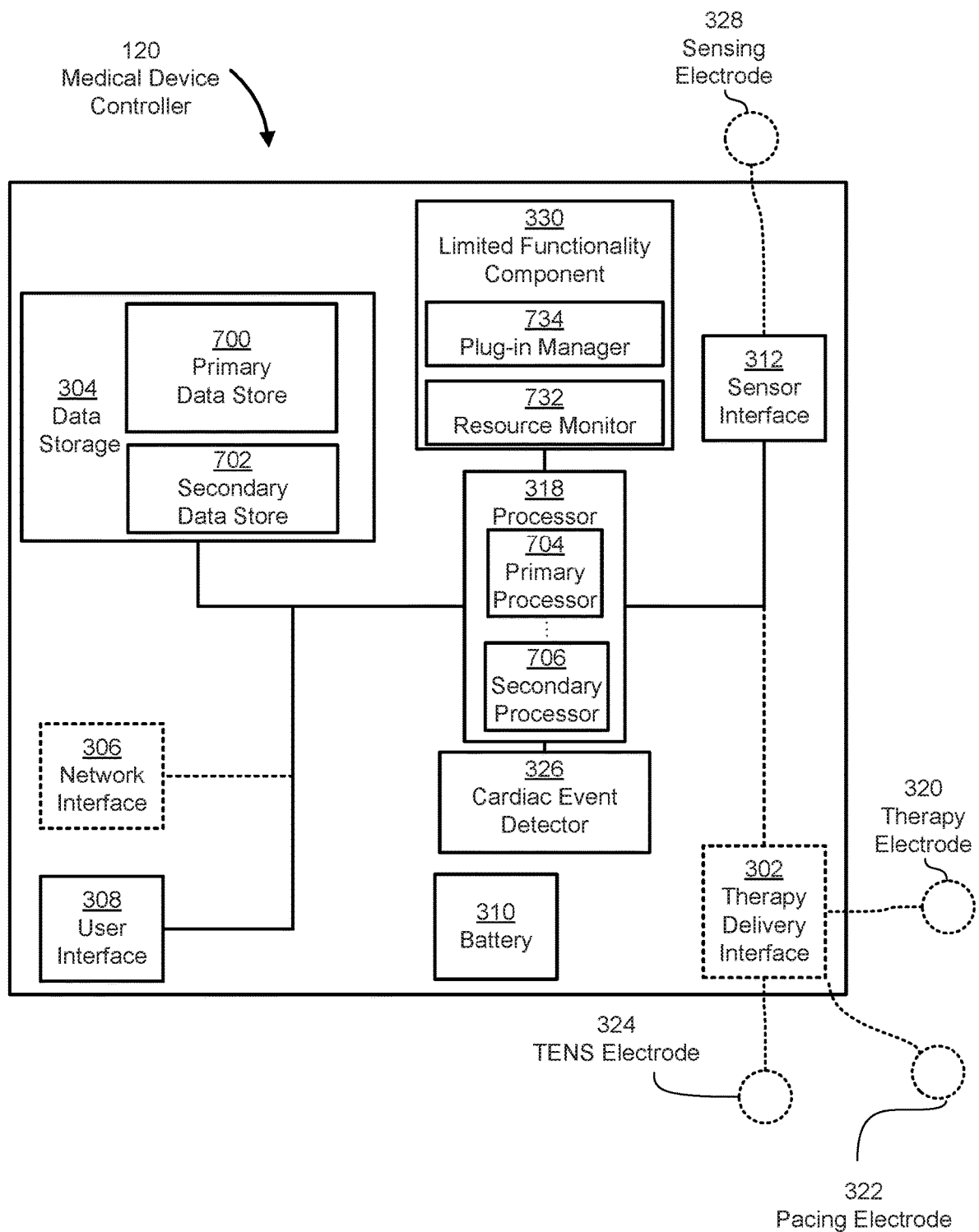
FIG. 7 is a schematic diagram of another example of a medical device controller.

FIG. 7 illustrates some example implementations that utilize isolated computing resources to support execution of a limited functionality component while preventing adverse effects on the primary operations of a medical device. As shown, FIG. 7 includes the controller 120, which operates generally as described above. However, in the controller 120 illustrated by FIG. 7, the data storage 304 includes primary data store 700 and secondary data store 702; the processor 318 includes at least two processors: a primary processor 704 and a secondary processor 706; and the limited functionality component 330 includes a resource monitor 732 and a plug-in manager 734. Examples may include any one or more of these features without departing from the scope of this disclosure.

In some examples in accord with FIG. 7, the limited functionality component 330 is implemented solely by one or more processors including the secondary processor 706. In these examples, the primary processor 706 and/or processors other than the one or more processors including the secondary processor 706 implement other components of the controller 120. This isolation of the limited functionality component from other components of the controller 120 protects the other components of the controller 120 from being affected by the limited functionality component.

In some implementations, one or more of the processors 318 is a discrete physical processor. In other implementations, one or more of the processors 318 is a distinct core of a single multicore processor. In some implementations, one or more of the processors 318 is a virtual processor implemented by one or more physical processors, each of which may be a single core or multicore processor. In at least one implementation, the processor 318 includes a power conserving processor arrangement as described in U.S. Pat. No. 8,904,214, titled "SYSTEM AND METHOD FOR CONSERVING POWER IN A MEDICAL DEVICE," issued Dec. 2, 2014 (hereinafter the "'214 Patent"), which is attached hereto as Appendix B and which is hereby incorporated herein by reference in its entirety. Other configurations of processors may be used to implement the isolation scheme described herein without departing from the scope of this disclosure.

In some examples, the primary data store 700 includes data related to primary operations of the controller 120. In these examples, the secondary data store 702 includes data related to limited functionality operations that are under control of the limited functionality component 330 (e.g., operations other than the primary operations). In some examples, the limited functionality component and/or the commands it executes exercise full control over data stored in the secondary data store 702 but are restricted to no access or read-only access of data stored in the primary data store 700. In these examples, other components of the controller 120 may exercise full control over data stored in the primary data store 700 and the secondary data store 702. In this way, components of the controller 120 other than the limited functionality component may manipulate data as needed to execute the primary operations of the controller without being affected by commands executed by the limited functionality component.

In some implementations, the primary data store 700 and the secondary data store 702 are different storage locations within a single physical data storage medium, such as a magnetic disk, flash memory, or RAM. In other implementations, the primary data store 700 and the secondary data store 702 are storage locations within discrete physical data storage mediums.

In at least one implementation, the primary data store 702 is implemented using the shared memory described in '214 Patent. As such, the limited functionality component may be configured to have only read-only access to the contents of the shared memory. For example, the shared memory may be used to store ECG data (e.g., 1-5 minutes or more ECG data). Accordingly, in some implementations, the limited functionality component may be configured to, during normal operation of the medical device, read and transmit the stored ECG data in a streaming manner to allow the communication device to receive and process such ECG data. Other configurations of data storage may be used to implement the isolation scheme described herein without departing from the scope of this disclosure.

In some examples, the medical device and the limited functionality component are configured so that the command set is executed using computing resources that are shared by the limited functionality component and the components configured to execute the primary operations of the medical device. In these examples, the limited functionality component is configured to comply with one or more computing resource policies.

These computing resource polices may be hardcoded (e.g. built into the programming of the limited functionality component and set at compile time) or data-driven (i.e. read in by the limited functionality component and set at runtime). In some examples, such policies may be written to a data file and downloaded to the medical device during a device update in the field. Such a scheme can allow for any desired or required security updates to medical devices in the field. In some cases, for increased security, policies and/or features affecting the limited functionality component of the medical device may not be updated in the field but be returned to a service center for any such updates during maintenance.

In some implementations, the limited functionality component includes the resource monitor 732. The resource monitor 732 is configured to cause the limited functionality component to comply expressly with a computing resource policy by actively monitoring and/or allocating the shared computing resources available for execution of the command set. Additionally, in some implementations, the limited functionality component is configured to comply inherently with a computing resource policy so that no monitoring is required. For instance, the programming of the limited functionality component may cause it to consume a limited amount of the shared computing resources without express reference to a computing resource policy. In either of these implementations, the limited functionality component and the command set are configured to utilize no more than a maximum amount of the shared computing resources. This maximum is sufficiently low so as to maintain a minimum amount of the shared computing resources that are dedicated to the primary operations of the medical device, thereby preventing any adverse effects to the primary operations. For example, such a maximum may be expressed as and stored as a percentage of the shared computing resources. For example, such a maximum may be expressed as and stored as a value representing the maximum shared resources (e.g., an amount of run-time memory storage in megabytes or gigabytes.)

In some implementations, the limited functionality component includes the plug-in manager 734. The plug-in manager 734 is configured to receive, validate, install, execute, upgrade, and/or uninstall plug-ins received from a communication device (e.g., the communication devices described below with reference to FIGS. 10 and 11) or other authorized source (e.g., directly from remote servers described in FIGS. 10 and 11). These plug-ins may extend the functionality of the limited functionality component 330. For instance, the plug-ins, once installed and operational, may enable the limited functionality component to process new and additional commands. These new commands may be entirely new functionality or may be built upon previously available commands.

Plug-ins may be distributed as any of a variety of component types. These types include stand-alone executables, libraries, and scripts. As such, the plug-ins may be written in C or C++ and may be statically or dynamically linked. Plug-ins that are distributed as libraries may implement a predefined API that the plug-in manager 734 is configured to call to execute the plug-in.

In one example, the plug-in manager is configured to validate a newly received plug-in by authenticating the source of the plug-in. This authentication may be executed using password authentication or certificated-based authentication. For instance, the plug-in may be signed by a trusted source's private key and verified by the plug-in manager 734 using the source's public key. One example of the use of plug-ins in conjunction with the limited functionality component 330 is described further below with reference to FIG. 12.

In some implementations, the limited functionality component is configured to protect the primary operations of the medical device by limiting execution of commands along various dimensions. This limitation may be a complete prohibition from executing a command, executing the command in a manner that consumes less computing resources (e.g., provide only heartbeat information rather than a full array of ECG data), executing the command less frequently than specified by the communication device, etc. For instance, according to one example, the limited functionality component is configured to execute only commands that are members of the limited functionality command set (i.e., only those command types that have been tested and proven to not adversely affect primary operations). In some examples, the limited functionality component may additionally be configured to limit execution of commands to: a threshold number of commands per time period, a threshold number of active commands, a threshold percentage of processor utilization, a threshold percentage of memory consumption, and a threshold number of threads. In some examples, the limited functionality component may additionally be configured to shut down execution of commands based on, e.g., transgressions relating to the threshold number of commands per time period, the threshold number of active commands, the threshold percentage of processor utilization, the threshold percentage of memory consumption, and the threshold number of threads. One or more such limits or shut down criteria can be configured by a user with administrator level access to a device interface of the medical device. It is appreciated that many other limits, shut down criteria, and/or modes of controlling the limited functionality component other than the examples given herein may be used. In some examples, the limited functionality component is configured to limit or shut down command execution based on processor type or based on an amount of power left in a battery, such as the battery 310. For instance, when executing according to this configuration, the limited functionality component may compare the amount of power left to one or more threshold values (e.g., 10% battery power remaining, 1 hour of power remaining, etc.) and prevent or terminate command execution.

In some implementations, the limited functionality component may be configured to limit or shut down command execution in a specific way during execution of other, identified operations. For instance, the limited functionality component may prevent execution of any command that affects the user interface of the medical device while the medical device is executing a treatment protocol. In some examples, a treatment protocol comprises device and user actions that are executed or performed when the medical device detects a treatable arrhythmia. For instance, when the arrhythmia is detected, a vibration alarm is activated which continues throughout the treatment protocol. Subsequently, a siren alert may be given. In some examples, if an arrhythmia is detected during a sleep period (e.g., when the patient is asleep), the vibration and siren alerts can be activated together. The user interface displays a message prompting a conscious patient to provide a response indicating that the patient is conscious, and as such the treatment may be suspended. This keeps inappropriate arrhythmia detections from becoming inappropriate shocks. For example, if the patient presses one or more "response" buttons disposed on the controller 120 at any time during the treatment sequence, the alerts stop and the treatment shock is delayed. If the patient does not respond, the device continues to give alerts and voice prompts to the patient and bystanders. The entire treatment protocol, from arrhythmia detection to delivery of the treatment shock, may take less than one minute. If the arrhythmia continues after the first treatment shock, a further shock may be delivered. In such situations, the limited functionality component may allow execution of commands that transmit data to the communication device for display by the communication device while the treatment protocol is ongoing.

In some implementations, the limited functionality component may include a web server that can be accessed via a secure authenticated session with the communication device. For example, the communication device may comprise a web browser or a web client configured to interact with the web server, using Internet Protocol (IP) and/or Hypertext Transfer Protocol (HTTP/HTTPS) and/or other similar protocols, as described herein. In some examples, the communication device may be limited to interacting with the medical device based on a type of protocol. For example, only web interactions using the web server based HTTP/HTTPS protocol outlined above may be permitted. In some implementations, other types of web service protocols such as REST, XML-RPC, SOAP, and JSON-RPC may be implemented.

Limited Functionality Command Set

The limited functionality command set may include commands that, when executed by the limited functionality component, perform a wide variety of actions. Table 1 lists some example commands in a command set according to at least one example.

TABLE 1

| Command | Description |
| --- | --- |
| Get (Element_ID) | Returns a value of the data element identified by Element_ID. |
| Set_Threshold (Value, Element_ID) | Creates an association between the specified Value and Element_ID. |
| Watch (Element_ID, Watch_Type, Report_Frequency) | Causes the limited functionality component to monitor the data element identified by the Element_ID according to the Watch_Type. Detected transgressions of the value of the data element will be reported to the address specified by the Watcher_Address at a frequency specified by the Report_Frequency. |
| Set_Watcher (Watch_ID, Watcher_Address) | Causes the limited functionality component to associate the watch identified by the Watch_ID with the Watcher_Address. Reports generated by the Watch_ID will be reported to the Watcher_Address. |
| Display_Message (Message_ID) | Causes the limited functionality component to request that the user interface of the medical device display a predefined message identified by the Message_ID. |
| Replace_Message (Message_ID, New_Message) | Causes the limited functionality component to replace the predefined message identified by the Message_ID with the New_Message. |
| Create_Message (New_Message) | Causes the limited functionality component to create a message with the content of New_Message. |
| Display_Object (Object_Address) | Causes the limited functionality component to receive an object stored on the communication device at the Object_Address and display the object via the user interface of the medical device. |

TABLE 1-continued

| Command | Description |
| --- | --- |
| Request_Method (Component_ID, Method_ID, Method_Args) | Causes the limited functionality component to call the Method_ID of medical device component identified by the Component_ID with the Method_Args, thereby requesting execution of the Method_ID with the Method_Args. |
| Filter_Data (Data, Filter_ID) | Causes limited functionality component to apply a filter (e.g., Low Pass, High Pass, Band Pass, Wavelet . . . ) identified by the Filter_ID to the Data before transmitting the data to the communication device |
| Correlate_Data (Data_Set_ID1, Data_Set_ID2) | Causes the limited functionality component to calculate and transmit a correlation of the two datasets identified by the Data_Set_ID1 and Data_Set_ID2s. |

Element_IDs identify data elements exposed by the limited functionality interface. Data elements may be retrieve via the limited functionality interface via the Get( ) command. These data elements may be stored in a data store (e.g., the primary data store 700 or the secondary data store 702) of the medical device. Data elements may be descriptive of various information regarding the patient, the medical device, the environment of the medical device, the communication device, the user of the communication device, and the environment of the communication device. More specifically, data elements may be descriptive of patient parameters (e.g., ECG data and heart sound data), predefined messages, new message, and/or modified messages. Data elements may also be descriptive of metrics indicative of a status of the medical device, such as electrode fall-off status; and other information regarding the patient or medical device, such as patient location data, patient name, and prescription compliance data. Other examples of specific data elements include images received from the communication device and metrics descriptive of the signal strength of a network connection between the medical device and the communication device and an amount of power remaining in a battery included in the communication device.

Commands, such as Display_Message( ), Replace_Message( ), Create_Message( ), and Display_Object( ), that affect the user interface of the medical device may be referred to herein as "interface commands." In some examples, the limited functionality component transmits interface commands to the user interface component for processing by the interface component. In some examples, the Replace_Message( ) interface commands is configured to determine whether the Message_ID_targeted for modification may be modified prior to execution the modification. In some examples, the Replace_Message( ) interface command makes this determination by identifying whether the message has been flagged as restricted. By referencing flags that potentially restrict access to particular messages, the Replace_Message( ) interface command is configured to be unable to affect primary operations of medical devices.

Commands, such as Correlate_Data( ) and Filter_Data( ), that manipulate data generated by operation of the medical device after completion of the operation and prior to transmitting the data to the communication device are referred to herein as "post process commands." As described above, the Filter_Data( ) command applies a filter to data generated by operation of the medical device. In this way, the Filter_Data( ) command may be used to remove outliers and other undesirable artifacts from data provided to the communication device. Also as described above, the Correlate_Data( ) calculates correlations between two or more data sets. For example, such a correlation can include correlation between ECG data and accelerometer data.

In some implementations, the components of the medical device that expose interfaces supporting the Request_Method( ) interface command include logic that determines whether the method identified by the Method_ID, if executed with the Method_Args, might affect a primary operation of the medical device. If such execution might affect any primary operation, the component will not execute the Method_ID. In this way, the Request_Method( ) interface command complies with an expressly or inherently implemented computing resource policy. In some embodiments, the resource monitor 732 monitors and enforces such computing resource policies, thereby freeing other components from this computational burden.

Other Virtualization Examples

In some implementations, the components of the medical device controller 120 may protect the primary operations of the controller 120 by executing a single operating system with two or more kernels (e.g., Xenomai operating system extension). In this implementation, the primary operations are serviced by a first kernel that executes one or more patient care components and the limited functionality operations are serviced by a second kernel that executes a limited functionality component (e.g., the limited functionality component 330). Further, in this implementation, the first kernel is executed with greater priority than the second kernel. In this way, the primary operations are isolated from and not affected by the limited functionality operations.

In some implementations, the components of the medical device controller 120 may protect the primary operations of the controller 120 by executing a supervisory operating system (e.g., a hypervisor) that manages subordinate operating systems. The hypervisor may be a "bare metal" hypervisor (i.e., a hypervisor that manages the computing hardware of the controller 120 directly), or a "hosted" hypervisor (i.e., a hypervisor that utilizes the services of another operating system that, in turn, manages the computing hardware of the controller. In these implementations, the primary operations are serviced by a first operating system that executes one or more patient care components and the limited functionality operations are serviced by a second operating system that executes the limited functionality component. Further, in this implementation, the first operating system is executed with greater priority than the second operating system. In this way, the primary operations are isolated from and not affected by the limited functionality operations.

Limited Functionality Interface Processes

Figure 8:
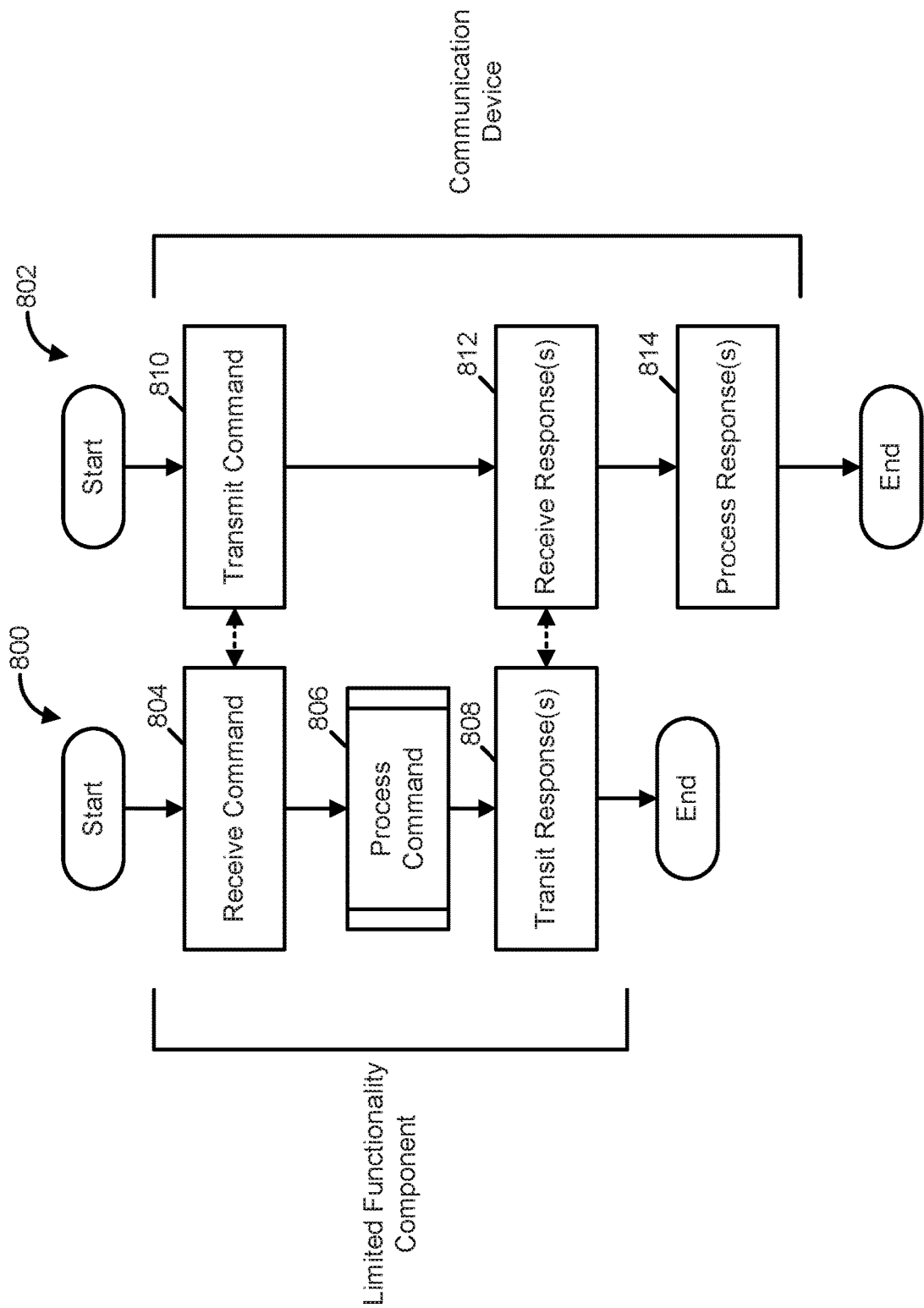
FIG. 8 is a flow diagram illustrating two examples of interface processes.

As described above, some examples execute one or more interface processes. FIG. 8 illustrates two such processes, an interface process 800 and an interface process 802. As shown, the interface process 800 is executed by a limited functionality component of a medical device, such as the limited functionality component 330. The medical device including the limited functionality component may be any medical device described herein. Also as shown, the interface process 802 is executed by a communication device, such as the communication device 800 described further below with reference to FIG. 8.

The interface process 802 starts in act 810, where the communication device transmits a command to the limited functionality component. This command may be any command from the command set executable by the limited functionality component and may be configured to not affect primary operations of the medical device. The communication device may be configured to be unable to issue commands other than those from the command set executable by the limited functionality component.

The interface process 800 starts in act 804, where the limited functionality component receives the command from the communication device. In act 806, the limited functionality component processes the command. One example of the acts executed by the limited functionality component within the act 806 is described further below with reference to FIG. 9.

In act 808, the limited functionality component transmits to the communication device one or more responses resulting from execution of the command and the interface process 808 ends. As described above, depending on the command executed, the response may include information generated by or stored on the medical device. In some examples, the response includes configuration information that enables the communication device to receive one or more on-going transmissions of information (e.g., streams generated by a Watch( ) command) from the limited functionality component. These on-going transmissions may be in response to a predetermined condition, substantially in real time, during an occurrence of the predetermined condition, in response to user input, in response to a predetermined triggering event, continuous over a period of time, substantially continuous over a period of time, during periodic time intervals, or during aperiodic time intervals.

In act 812, the communication device receives the one or more responses. In the act 814, the communication device processes the response and the interface process 802 ends. Interface processes in accord with the interface process 800 and 802 enable a medical device to share information with one or more communication devices without impacting primary operations of the medical device.

Figure 9:
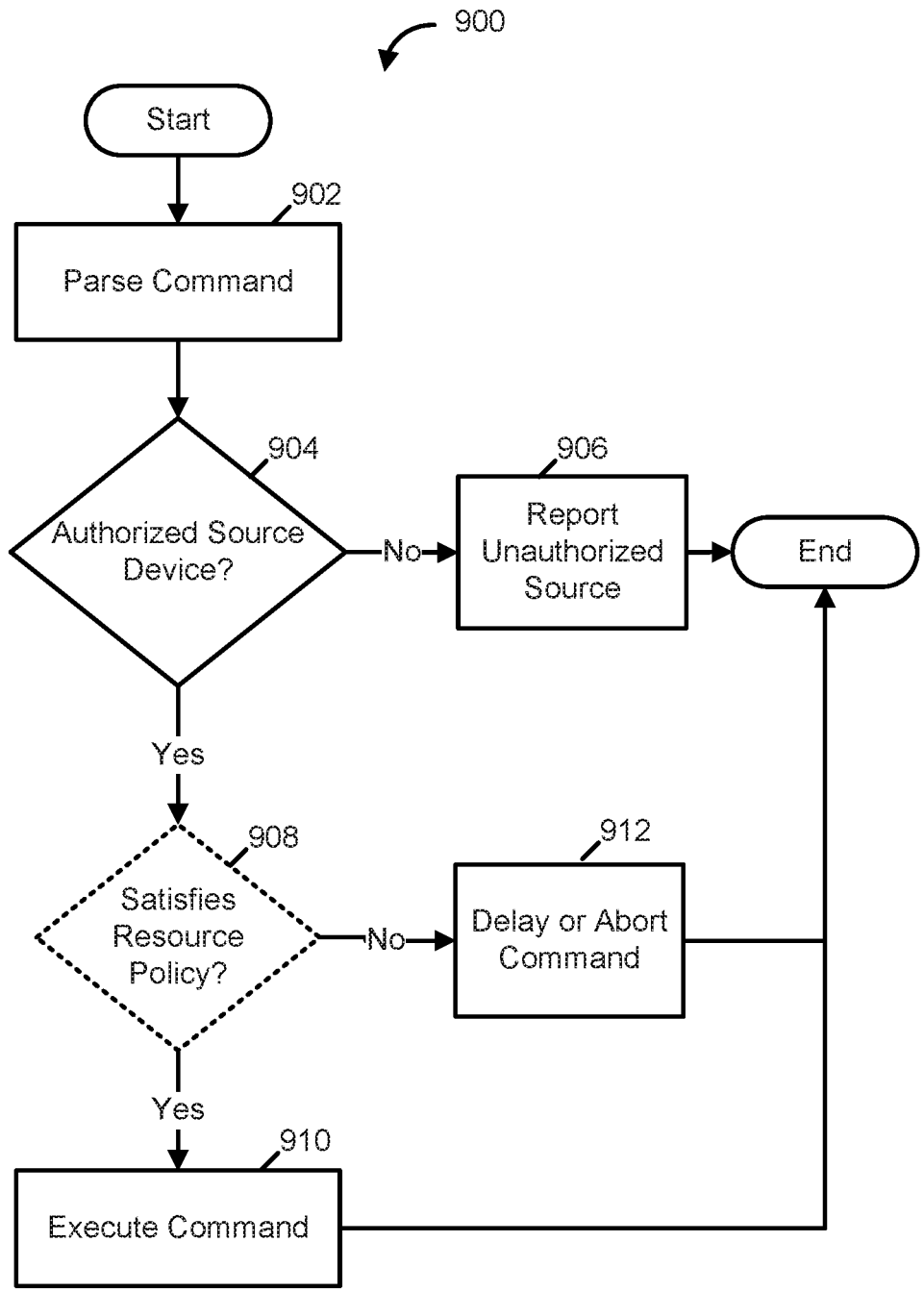
FIG. 9 is a flow diagram illustrating one example of a command processing process.

As described above, some examples execute one or more command processing processes. FIG. 9 illustrates one such process, a command processing process 900. As shown, the process 900 is executed by a limited functionality component of a medical device, such as the limited functionality component 330. The medical device including the limited functionality component may be any medical device described herein or a different type of medical device.

The process 900 starts in act 902, where the limited functionality component parses the command to identify the command type and command arguments. In act 904, the limited functionality component determines whether the communication device that originated the command (e.g. the communication device 800 described further below with reference to FIG. 8) is an authorized communication device. In at least one example, the limited functionality component makes this determination by first authenticating the identity of the communication device and then determining whether the identity of the communication device has been previously identified and granted authorization to execute the command. The identity of the communication device may be authenticated using password authentication or certificated-based authentication, among other mechanisms. If the communication device is authorized to request execution of the command, the limited functionality component executes act 906. If the communication device is not authorized to request execution of the command, the limited functionality component executes act 908 or act 910.

In the act 908, which is optional, the limited functionality component determines whether execution of the command complies with all applicable computing resource policies. The act 708 is performed only by examples that expressly load and evaluate computing resource policies. In these examples, the limited functionality component implements the resource monitor 732 to evaluate the computing resource policies. For instance, in one example, a computing resource policy requires that each computing resource utilized by limited functionality operations must be less than a corresponding threshold value of a set of threshold values. Each threshold value of the set of thresholds represents a different computing resource of the medical device. In some examples, the set of threshold values includes a threshold value for compute resources, a threshold value for data storage resources, and a threshold value for battery power. In these examples, the resource monitor predicts the total computing resources of each type to be consumed by all limited functionality operations, should the limited functionality component execute the command. If none of the predicted resource utilization values exceed its corresponding threshold value, execution of the command is in compliance with the computing resource policy. Other computing resource policies may be evaluated by the resource monitor 732. The examples disclosed herein are not limited to any particular resource policy.

If execution of the command complies with all applicable computing resource policies, the limited functionality component executes the act 910. If execution of the command does not comply with all applicable computing resource policies, the limited functionality component executes act 912.

In the act 906, the limited functionality component reports the attempt to execute a command by the unauthorized communication device and terminates execution of the command execution process 900. For instance, the limited functionality component may report the authorized communication device's attempt by displaying a notification on a user interface (e.g., the user interface 308) of the medical device or by transmitting a notification to a remote device.

In the act 912, the limited functionality component delays or aborts execution of the command and terminates the command execution process 900. Whether the execution of the command is delay or aborted in the act 912, may depend on a variety of factors including the values of one or more configurable variables of the medical device, the command type, the command arguments, and the identity and authorization of the communication device. Further, in some examples, the limited functionality component may report the delay or aborted command by displaying a notification on a user interface (e.g., the user interface 308) of the medical device or by transmitting a notification to a remote device (e.g., the communication device).

Notification Systems

As described above, in some examples, the limited functionality component is in data communication with one or more communication devices. FIG. 10 illustrates a notification system 1000 in accord with some of these examples. As shown, the notification system 1000 includes a medical device 1002, a communication device 1004, a remote server 1012, a network connection 1006 and a communication network 1014. The medical device 1002 exchanges information with the communication device 1004 via the network connection 1006. Similarly, the communication device 1004 may exchange information with the remote server 1012 via the network 1014. In at least one example, the remote server 1012 is configured to deploy one or more components (e.g., programs or "apps") to the communication device 1004 that cause the communication device 1004 to transmit particular commands to the medical device 1002.

The network connection 1006 may be implemented through any one or combination of wireless communication standards and protocols including, for example, BLUETOOTH, Wireless USB, ZigBee, and Wireless Ethernet. The network 1014 may include any communication network through which programmable devices may exchange information. In some examples, the network 1014 supports wireless network and/or wired connections. For instance, the network 1014 may support any of various networking standards such as GSM, CMDA, USB, BLUETOOTH, CAN, ZigBee, Wireless Ethernet, and TCP/IP among others.

Figure 10:
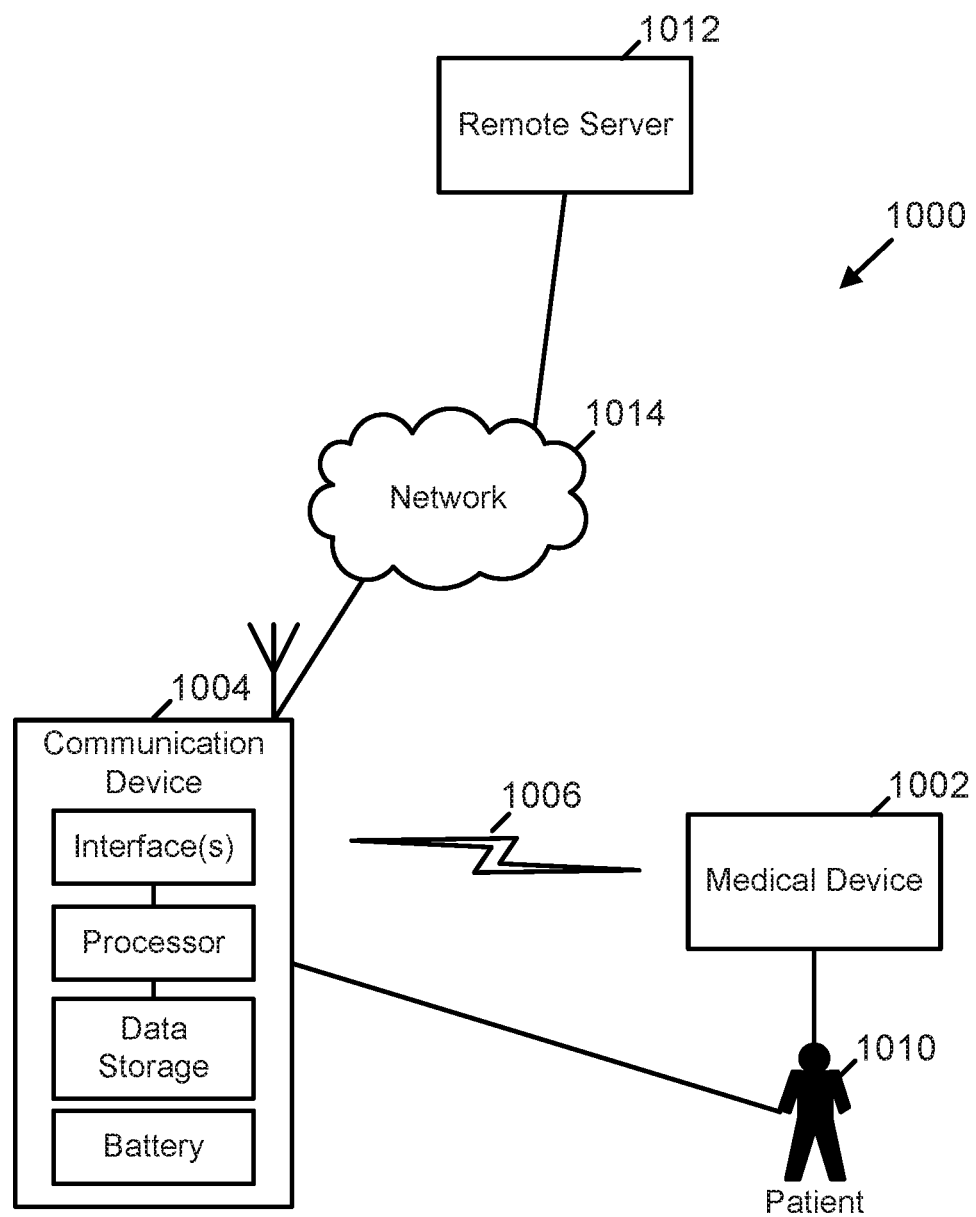
FIG. 10 is a block diagram of one example of a notification system.

The medical device 1002 may include any medical device disclosed herein or a different medical device that includes a limited functionality component for facilitating the interactions shown in FIG. 10. In one example illustrated by FIG. 10, the medical device 1002 is associated with and provides care to a patient 1010. In this example, the communication device 1004 is also associated with and provides information to the patient 1010. For example, the communication device 1004 may be incorporated into a base station and/or medical device charger unit placed in the patient's home or other convenient location, e.g., similar to the base station system shown in and described in connection with FIG. 4. Accordingly, the communication connection 418 of FIG. 4 is similar to the network connection 1006 of FIG. 10. In some implementations, the communication device 1004 may be releasably secured and/or coupled into a receptacle of the base station as described above.

In various examples, the communication device 1004 is implemented using any of a variety of programmable devices (e.g., a device with data storage and at least one processor in data communication with the data storage). In some examples, the communication device 1004 includes a plurality of interfaces, one or more processors, and a data storage device coupled to one another via a communication mechanism, such as a bus. In these examples, the communication device 1004 also includes a battery to power the device and may include one or more antennas. The plurality of interfaces in the communication device 1004 include a user interface, a network interface configured to communicate with the network 1006, and a medical device interface configured to exchange information with the medical device. This information may include one or more limited functionality commands.

Particular examples of the communication device 1004 include medical devices (e.g., in FIG. 10, medical devices other than medical device 1002), wearable devices, medical device chargers, medical device base stations, smart phones, tablet computers, and laptop computers. Wearable devices that may serve as the communication device 1004 include various garments with integrated technologies, watches, anklets, necklaces, belt buckles, and glasses.

In examples where the communication device 1004 is implemented via a smart phone, a dedicated software application (or an "app") may be downloaded to the smart phone to facilitate the interactions described herein. In some examples, as an enhanced security measure, the communication device 1004 is configured to automatically and exclusively execute such an application when the communication device 1004 is connected to a power source or when the communication device 1004 powers up. In such examples, the smart phone operates solely as the communication device 1004 for enabling the communications and interactions described herein. For example, the smart phone may be configured to operate in a "kiosk mode" and display only minimal information on the user interface during such operation. For instance, the application may be written for an Android, iOS, Windows, or other operating system of the smart phone.

In some examples, the communication device 1004 is included within a housing structure of the medical device 1002. As such, the limited functionality component can communicate with the communication device 1004 through one or more communication mechanisms incorporated within the integrated circuitry of the medical device 1002.

In some examples, the communication device 1004 is configured to act as an information conduit (or "hotspot") for the medical device 1002 by exchanging information regarding the medical device 1002, the patient 1010, and the environment of the medical device 1002 with a remote server 1012 via a communication network 1014. For example, in an implementation where the communication device 1004 is configured as an information conduit, the communication device 1004 is configured to pass data between the medical device 1002 and the remote server 1012 without modifying the data. In certain cases, the device 1004 may perform certain limited transformations on the data prior to relaying the data to the remote server 1012 (or to the medical device 1002 if the data is being transmitted from the remote server 1012).

In some examples, the communication device 1004 can establish an authenticated and secure connection over the network 1014 via another computing device (e.g., a desktop workstation, laptop workstation, tablet or other such device). For example, the user may cause the communication device 1004 (e.g., a smart phone) to establish a wired (e.g., USB connection) or wireless connection (e.g., BLUETOOTH connection) with the other computing device to connect to the remote server 1012.

In some examples, the communication device 1004 may vary its operation based on whether or not it has connectivity to the network 1014. For instance, if the communication device 1004 has no or limited network connectivity (e.g., no or limited cellular network connectivity), the medical device data can be stored to a local storage component on the communication device 1004. For instance, the local storage component can be an SD card or an embedded storage device in the device 1004. The data can be stored in an encrypted format that is compliant with patient data security requirements. This locally stored data can be transmitted to the remote server 1012 when connectivity is restored. For instance, a patient carrying the communication device 1004 may be able to either carry the device 1004 to an area with better signal strength or hand the device over to another user who can travel to such an area. In some implementations, the patient and/or other user may use a wired or wireless connection to another computing device (e.g., a desktop workstation, laptop workstation, tablet or other such device) that can establish a connection to the network 1014 to cause the transmission of the data to the remote server 1012.

For example, the communication device 1004 can include a callback mechanism registered and called by the operating system of the device 1004 to monitor the available network signal strength. For example, in the Android operating system, a signal strength monitoring component can be included. The signal strength monitoring component can be configured with one or more predetermined criteria indicating, for example, a minimum threshold signal strength that may be available before the data can be transmitted to the remote server 1012. Other criteria can be based on, for example, confirming the stability of the signal strength over a period of time. As such, the signal strength monitoring component can verify that the signal strength maintains a threshold strength for a certain amount of time, and/or verify that connectivity to the network is available, before the transfer of stored information is initiated. In an implementation, an example mechanism to send the stored data from the device 1004 to the remote server 1014 can be based on the UFTP file transfer protocol.

In some examples, the communication device 1004 has two modes of operation: internal and external. The internal mode is designed for use with a communication device 1004 where the communication device 1004 is enclosed in the housing structure of the medical device 1002. In some examples, such enclosure completely hides the communication device 1004 from external view. In some examples, when executing in internal mode, the communication device 1004 is configured to automatically power down when not in use and/or when disconnected from a power source. In some implementations, the communication device 1004 may include a dedicated power source. For example, such a power source can be a rechargeable battery, e.g., a Li-Ion based battery power supply. In some examples, the power source can be a non-rechargeable battery.

In contrast to the internal mode, the external mode is designed for use with a communication device 1004 where the communication device 1004 is visible and accessible to the patient 1010. For example, a user interface disposed on the communication device 1004 may display status information relating to the communication device 1004 and any ongoing communication exchange(s) as described herein.

According to some examples, the communication device 1004 can be configured to automatically setup communications between the medical device 1002 and the remote server 1012. In these examples, the communication device 1004 is further configured to display information regarding its operation and data communications via a user interface of the communication device 1004 but restrict user interaction with the user interface. In some implementations, the user may only be able to power on or off the device. In other implementations, the user may only be able to control screen brightness and timeouts. The operation and data communication information displayed may include battery level, connection strength to the network 1014, status of connectivity between the communication device 1004 and the medical device 1002 including, in some cases, status information for any ongoing communications, and version information for the hotspot component. The communication device 1004 may transmit the operation and data communication information to the remote server 1012. Additionally, the communication device 1004 may transmit information descriptive of its location to the remote server 1012 (e.g., GPS coordinates or other position/location details). In some examples, the communication device 1004 is configured to transmit information descriptive of the connection strength to the medical device 1002. Further, in some examples, the communication device 1004 is configured to establish a firewall that will inhibit any unauthorized connections to the medical device 1002. The firewall can be configured to inhibit any connections to the medical device 1002 other than through the communication device 1004. In some examples, the communication device 1004 is configured to log errors in the data storage of the communication device 1004 (or a storage in some other location on the network).

In some examples, the communication device 1004 is configured to automatically execute as a hotspot component when the communication device 1004 is connected to a power source or when the communication device 1004 powers up. Also, in these embodiments, the communication device 1004 is configured to exclusively execute the hotspot component. In various implementations, the communication device 1004, when configured as the hotspot component or otherwise, complies with 21 CFR § 880.6310 which defines a Medical Device Data System (MDDS). In one example, the communication device 1004 comprises hardware or software products that can be configured to transfer, store, convert formats, and display medical device data. In such examples, the communication device 1004 can be configured, using the techniques and systems described herein, to not modify the data, modify the display of the data, and/or control the functions or parameters of the medical device or any other medical device.

Two additional examples in which the limited functionality component and the communication device interoperate to achieve certain benefits will now be described. In a first example, the medical device 1002 includes a wearable defibrillator. Further, in this example, the patient 1010 is fitted with the medical device 1002 and is prescribed an exercise and/or activity regimen (e.g., in connection with a medical rehabilitation program). Compliance with the regimen requires the patient 1010 to perform, e.g., certain actions in accord with a prescribed treatment schedule. The prescribed treatment schedule may, in some cases, require the patient 1010 to exercise for 30 minutes each day and/or take medication three times a day. In this example, a primary operation of the medical device 1002, which is a wearable defibrillator, may be to monitor and treat the patient 1010 in the event a cardiac arrhythmia is detected at any point in time, including while the patient 1010 is complying with the regimen.

Continuing this example, the patient 1010 and/or a physician at a remote location (accessible via the network 1014) wishes to be notified if certain patient parameters transgress one or more configurable threshold values. More specifically, the patient 1010 and/or the physician wishes to be notified if the patient's heart rate exceeds 180 bpm or the elapsed time since last compliance with the treatment schedule exceeds 1 day. To configure the notification system 1000 to notify the patient 1010 and/or the physician where these patient parameters transgress these threshold values, the patient 1010 interacts with a user interface of the communication device 1004. Alternatively, the physician may interact with a network device in communication with the remote server 1012 to configure the notification system 1000. This interaction results in the communication device identifying several commands that, when executed by a limited functionality component, will collectively configure the threshold values for the patient parameters described above. In response to identifying these commands, the communication device transmits, via a network interface of the communication device, requests including the commands to a limited functionality component (e.g., the limited functionality component 330) of the medical device 1002.

In this example, the limited functionality component receives the requests and, in response to such receipt, parses the requests to identify the commands, the patient parameters, and the threshold values. Next, the limited functionality interface executes the identified commands to store an association between the threshold values and the patient parameters.

In this example, the limited functionality component, as part of executing the identified commands, also stores an address of a recipient device to which notifications will be transmitted. This recipient device may be the communication device 1004 or some other device in data communication with the network 1014.

In some examples, the communication device 1004 can be configured to transmit one or more requests to execute one or more limited functionality commands to the medical device 1002 and relay the results of those commands to a device at a remote location (e.g., accessible over the network 1014). For example, a physician may wish to be notified on his/her own handheld device when the patient's heart rate exceeds a threshold value during performance of a prescribed regimen. For example, a physician may wish to be notified on his/her own handheld device in the event a patient has an arrhythmia event during performance of a prescribed regimen.

In another example, the communication device 1004 can be configured to transmit one or more requests to the limited functionality component to execute one or more commands that, when executed, configure the limited functionality component to transmit notifications to the communication device 1004 and/or the remote server 1012 in response to detecting a predetermined trend or pattern in the underlying data. For example, when executing according to this configuration, if the patient's heart rate increases over a period of time, the limited functionality component can transmit a notification regarding the upward trend or pattern. In another example, the limited functionality component can be configured to transmit a notification describing a low range of heart rate variability detected over a specified period of time. Thus, in some examples, the limited functionality component is configured to transmit notifications in response to a pattern detected in an underlying patient parameter rather than a single triggering value.

Additionally, in this example, the limited functionality component, as part of executing the identified commands, starts a watch that monitors the patient parameters, and transmits a notification to a recipient device (e.g., the communication device 1004 or other device connected to the network 1014) if any of the patient parameters transgresses its corresponding the threshold value and/or if any underlying patient parameters change in accordance to one or more predetermined trends or patterns.

Also, in this example, the limited functionality component, as part of executing the identified commands, requests that the user interface component prompt the patient 1010 for information regarding compliance with the treatment schedule and return any information received in response to the prompt. More particularly, in this example, the limited functionality interface requests that the user interface prompt the user to indicate whether the user has taken their medication according to the treatment schedule. In response to receiving returned information from the user interface indicating that the user has not complied with the treatment schedule or in response to determining that the user has not complied via other mechanisms (e.g., by monitoring patient parameter values), the limited functionality component transmits a notification to the communication device 1004.

In response to receipt of a notification, the communication device 1004 processes the notification and alerts the patient 1010 and/or the physician of the value of the patient parameters. In this example, the alerts may indicate that the patient's heart rate has exceeded 180 bps and that the patient has not complied with the treatment schedule for 1 day.

Figure 12:
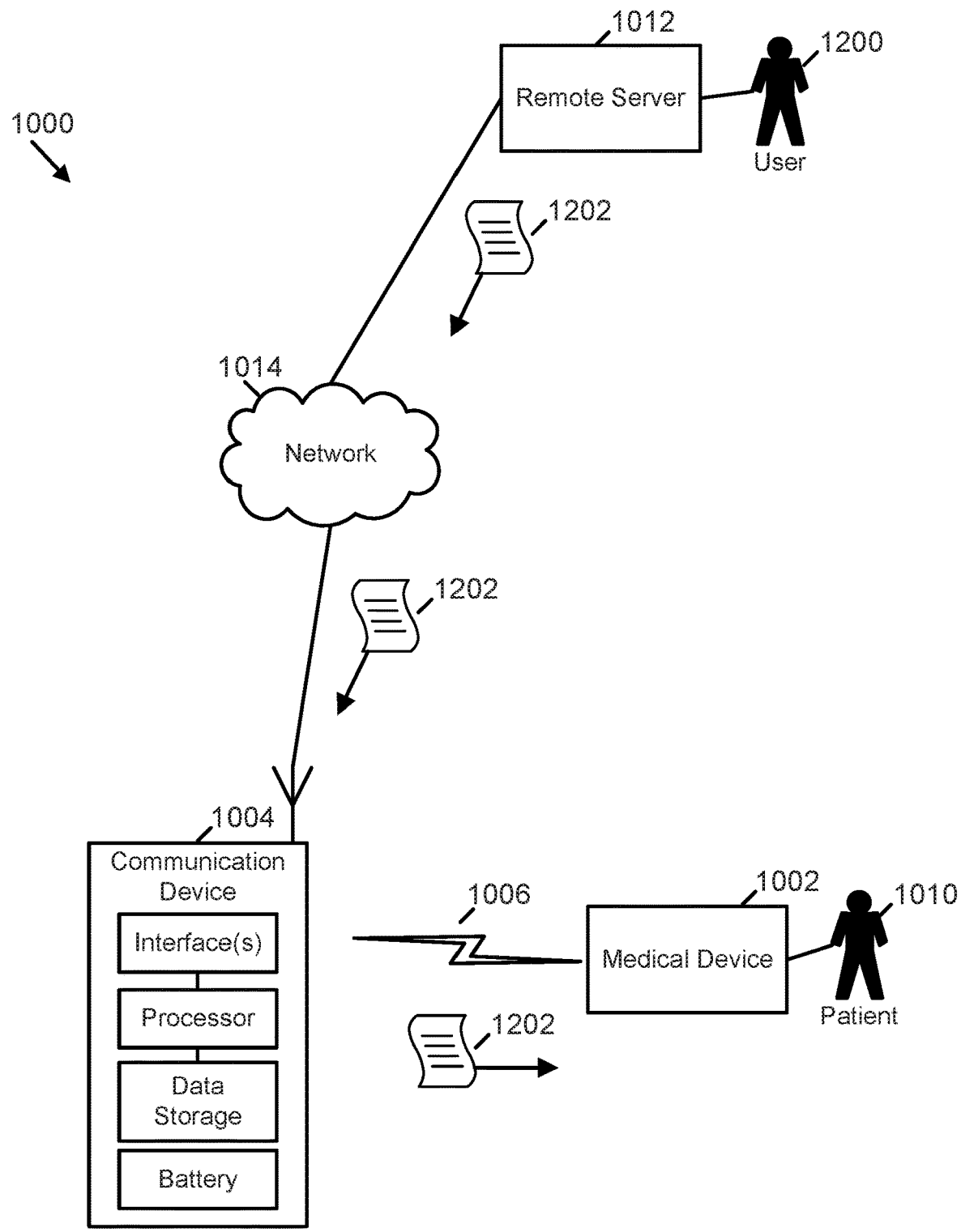
FIG. 12 is a block diagram of another example of a notification system.

In a second example illustrated by FIG. 12, the notification system 1000 is used to distribute a heart rate variability plug-in 1202 to the medical device 1010. As shown, the notification system 1000 illustrated in FIG. 12 includes generally the same components as, and functions generally in the same way as, the notification system 1000 illustrated in FIG. 10.

In this example, a user 1200 authors and selects the plug-in 1202 for distribution to the medical device 1002. The plug-in 1202 is configured to monitor the heart rate variability of the patient 1010 over time. As described above, the plug-in 1202 may take the form of a script, stand-alone executable, or library, among other forms. When executing according to its configuration, the heart rate variability plug-in 1202 tracks the heart rate of the patient over a configurable time window and transmits one or more notifications to the communication device 1004 on detecting the occurrence of certain heart rate or variability triggering criteria and/or changes, trends, or patterns in the underlying heart rate or variability. Further, in this example, the communication device 1004 may transmit any such notifications received from the medical device 1002 to the remote server 1012 via the network connection 1014. In some examples, the plug-in 1202 may be configured to exchange information, including transmitting such notifications, directly with the remote server 1012. These notifications are thereby available for review by the user 1200 and/or a physician. In at least one example, the user 1200 is a physician or other care provider.

As shown in FIG. 12, responsive to the user 1200 selecting the plug-in 1202 for distribution, the remote server transmits the plug-in to the communication device 1004 via the network 1014. The communication device 1004 receives the plug-in 1202 and, in response, transmits the plug-in 1202 to the medical device 1002 via the network connection 1006.

In response to receiving the plug-in 1202, a plug-in manager (e.g., the plug-in manager 734) authenticates the source of the plug-in 1202 as a trusted source, installs the plug-in, and executes the plug-in within the framework of a limited functionality component (e.g., the limited functionality component 330). It is appreciated that, in some examples, the plug-in manager may install the plug-in but not execute it. In these examples, the limited functionality component may execute the program, for example, after receiving a command implemented partially or completely by the plug-in. In this way, the functionality of the limited functionality component may be extended in a convenient, but secure, manner.

Figure 11:
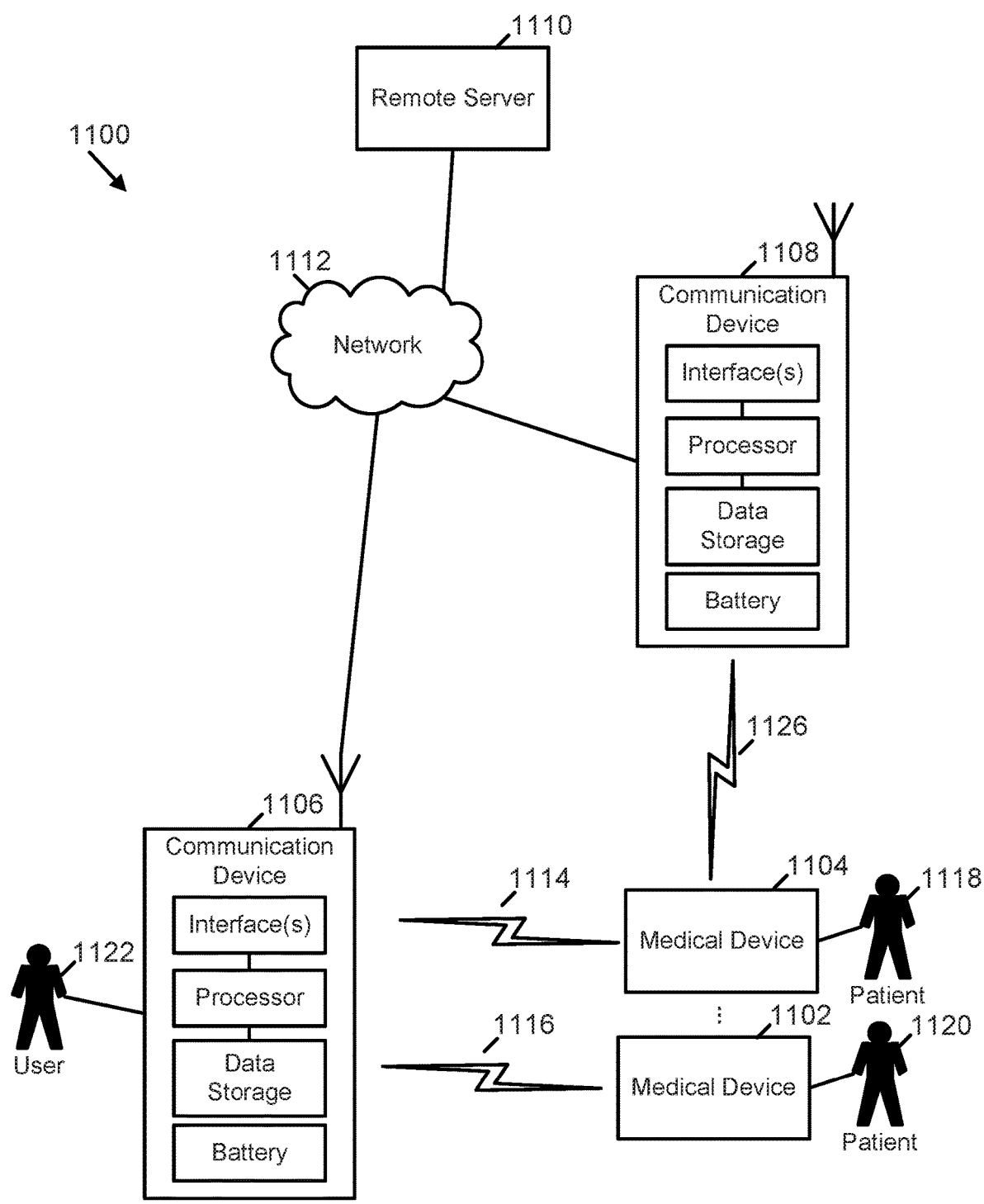
FIG. 11 is a block diagram of another example of a notification system.

FIG. 11 illustrates a notification system 1100 in accord with some of examples. As shown, the notification system 1100 includes medical devices 1102 and 1104, communication devices 1106 and 1108, a remote server 1110, a communication network 1112, and network connections 1114 and 1116. The medical device 1102 exchanges information with the communication device 1106 via the network connection 1116. Similarly, the medical device 1104 exchanges information with the communication devices 1106 and 1108 via the network connections 1114 and 1126. In this example, the communication devices 1106 and 1108 exchange information with the remote server 1110 via the network 1112.

The network connections 1114, 1116, and 1126 may be implemented through any one or combination of wireless communication standards and protocols including, for example, BLUETOOTH, Wireless USB, ZigBee, and Wireless Ethernet. The network 1112 may include any communication network through which programmable devices may exchange information. In some examples, the network 1112 supports wireless network and/or wired connections. For instance, the network 1112 may support any of various networking standards such as GSM, CMDA, USB, BLUETOOTH, CAN, ZigBee, Wireless Ethernet, and TCP/IP among others.

The medical devices 1102 and 1104 may include any medical device disclosed herein or a different medical device that includes a limited functionality component. In one example illustrated by FIG. 11, the medical device 1102 is associated with and provides care to a patient 1120 and the medical device 1104 is associated with and provides care to a patient 1118. In this example, the communication device 1106 is associated with and provides information to a user 1122, and the communication device 1124 is associated with and provides information to the patient 1118.

As illustrated in FIG. 11, a medical device may communicate with one or more communication devices and a communication device may communicate with one or more medical devices. In some examples, a single communication device may communicate with only one medical device at a time (e.g., be paired with only a single medical device at a time) and be disconnected or "unpaired" from a first medical device before connecting to a second medical device. For example, such a communication device may be paired over BLUETOOTH with a corresponding medical device. In some examples, the communication device may be configured to communicate with two or more medical devices without being disconnected from either medical device during a transmission. For example, such a communication device may be paired over BLUETOOTH with a plurality of medical devices using, e.g., BLUETOOTH multi-device convertibility. Coupling a single communication device with a plurality of medical devices may be advantageous where, for example, a care provider (e.g. the user 1122) monitors a plurality of patients.

In one example, the care provider may be a nurse in a hospital setting, and the patients 1118 and 1120 may both be ambulatory and engaged in rehabilitation regimens. In this situation, the nurse can monitor both patients' activities using a single communication device (e.g. a tablet computer) and can issue a reminder to either or both of the patients 1118 and 1120 should their heart rate exceed a threshold value. This reminder may instruct the patients 1118 and 1120 to stop exercising. In at least one example, this notification is initiated by the nurse via the communication device 1106 and is displayed by the either or both medical devices 1102 and 1104. In another example, coupling a single medical device with a plurality of communication devices may be advantageous where, for example, a patient (e.g. the patient 1118) and a care provider (e.g., the user 1122) both monitor the activity of the patient 1118. In this situation, the care provider 1122 can monitor both patients' activities using a single communication device (e.g. a tablet computer) and can configure the notification system to issue a notification should any of the monitored patients' 1118 and 1120 activities transgress preset thresholds and/or changes, trends, or has a pattern in accordance with preset changes, trends, or patterns in the underlying parameters. This example provides redundancy of monitoring activities, thereby increasing the safety afforded to the patient 1118 by the notification system 1100.

The processes disclosed herein each depict one particular sequence of acts in a particular example. The acts included in these processes may be performed by, or using, one or more computer systems specially configured as discussed herein. Some acts are optional and, as such, may be omitted in accord with one or more examples. Additionally, the order of acts can be altered, or other acts can be added, without departing from the scope of the systems and methods discussed herein. Furthermore, as discussed above, in at least one example, the acts are performed on a particular, specially configured machine, namely a medical device configured according to the examples disclosed herein.

Having thus described several aspects of at least one example, it is to be appreciated that various alterations, modifications, and improvements will readily occur to those skilled in the art. For instance, examples disclosed herein may also be used in other contexts. Such alterations, modifications, and improvements are intended to be part of this disclosure, and are intended to be within the scope of the examples discussed herein. Accordingly, the foregoing description and drawings are by way of example only.

The invention claimed is:

1. A communication device comprising:
   a battery configured to provide power to the communication device;
   a user interface;
   a network interface;
   a medical device interface configured to communicate with a medical device;
   a data storage; and
   at least one processor operably coupled to the user interface and the medical device interface and being configured to
      transmit, via the medical device interface, at least one command to a limited functionality component of the medical device, the at least one command configured to be processed by the limited functionality component of the medical device to monitor a patient parameter and not affect one or more primary operations of the medical device,
      receive, via the medical device interface without affecting the one or more primary operations, one or more values of the patient parameter from the limited functionality component of the medical device,
      analyze the one or more values, and
      display, via the user interface, information descriptive of the one or more values.

2. The communication device of claim 1, wherein the patient parameter comprises patient heart rate as determined by the medical device based on signals received from one or more sensors operably coupled to the medical device, and the information descriptive of the one or more values comprises a heart rate trend over a period of time.

3. The communication device of claim 1, the network interface being configured to communicate with a remote computer, wherein the at least one processor is configured to transmit the one or more values to the remote computer via the network interface.

4. The communication device of claim 3, the at least one processor being configured to receive, from the remote computer via the network interface, a remote command to display an instruction to a patient and to display the instruction to the patient via the user interface.

5. The communication device of claim 1, wherein the at least one processor is configured to select the at least one command from a predetermined set of commands stored on the data storage.

6. The communication device of claim 1, wherein the at least one command is configured to use secondary resources of the medical device that do not affect the one or more primary operations of the medical device.

7. The communication device of claim 6, wherein the secondary resources comprise resources of the medical device that are isolated from computing resources used to perform the one or more primary operations of the medical device.

8. The communication device of claim 1, wherein the at least one command is configured to have a lower execution priority than the one or more primary operations of the medical device.

9. The communication device of claim 1, wherein the communication device provides an identity of the communication device to the limited functionality component and the limited functionality component determines whether the identity of the communication device has been previously authorized prior to executing the at least one command.

10. The communication device of claim 9, wherein the at least one command is configured to comply with a level of authorization of the communication device.

11. The communication device of claim 1, wherein the patient parameter comprises at least one of blood oxygen levels, lung sounds data, blood pressure information, electrocardiogram data, physical activity data, patient symptom data, medication data, and heart sounds data.

12. The communication device of claim 1, wherein the at least one processor being configured to analyze the one or more values comprises the at least one processor being configured to identify a notification in the one or more values of a change in the patient parameter.

13. The communication device of claim 12, wherein the information descriptive of the one or more values comprises information related to changes in the patient parameter.

14. A communication device comprising:
a battery configured to provide power to the communication device;
a user interface;
a network interface;
a medical device interface configured to communicate with a medical device that is monitoring a cardiac condition of a patient;
a data storage; and
at least one processor operably coupled to the user interface and the medical device interface and being configured to
generate at least one command configured to request a response from the medical device that is monitoring the cardiac condition of the patient,
transmit, via the medical device interface, the at least one command to a limited functionality component of the medical device, the at least one command requesting the response from the medical device while at least one patient care component of the medical device performs one or more primary operations of the medical device during the monitoring of the cardiac condition of the patient,
receive, via the medical device interface during operation of the one or more primary operations, the requested response from the limited functionality component of the medical device,
analyze the response from the medical device, and
display, via the user interface, information descriptive of the response from the medical device.

15. The communication device of claim 14, wherein the response from the medical device comprises operational status information for the medical device.

16. The communication device of claim 14, wherein the response from the medical device comprises information relating to at least one of blood oxygen levels, lung sounds data, blood pressure information, electrocardiogram data, medication data, and heart sounds data of the patient.

17. The communication device of claim 14, wherein the response comprises information related to patient compliance with a treatment schedule.

18. The communication device of claim 14, wherein the response comprises information recorded by the medical device and related to an identified symptom being experienced by the patient.

19. The communication device of claim 14, wherein the at least one processor being configured to generate at least one command comprises the at least one processor being configured to select the at least one command from a predetermined set of commands.

20. The communication device of claim 14, wherein the communication device provides an identity of the communication device to the limited functionality component and the limited functionality component determines whether the identity of the communication device has been previously authorized prior to executing the at least one command.

21. A method comprising:
generating, by a processor of a communication device, at least one command configured to request a response from a medical device operably coupled to the communication device via a medical device interface;
transmitting, by the processor of the communication device via the medical device interface, the at least one command to a limited functionality component of the medical device, the at least one command requesting the response from the medical device while at least one patient care component of the medical device performs one or more primary operations of the medical device;
receiving, by the processor of the communication device via the medical device interface during operation of the one or more primary operations, the response from the limited functionality component of the medical device;
analyzing, by the processor of the communication device, the response from the medical device; and
displaying, by the processor of the communication device via a user interface operably coupled to the processor of the communication device, information descriptive of the response from the medical device.

22. The method of claim 21, wherein receiving the response from the limited functionality component comprises receiving a response comprising operational status information for the medical device.

23. The method of claim 21, wherein receiving the response from the limited functionality component comprises receiving a response comprising at least one of blood oxygen levels, lung sounds data, blood pressure information, electrocardiogram data, physical activity data, patient symptom data, medication data, and heart sounds data.

24. The method of claim 21, wherein receiving the response from the limited functionality component comprises receiving a response comprising information related to patient compliance with a treatment schedule.

25. The method of claim 21, wherein receiving the response from the limited functionality component comprises receiving a response comprising information recorded by the medical device and related to an identified symptom being experienced by the patient.

26. The method of claim 21, wherein receiving the response from the limited functionality component comprises receiving a response comprising one or more values of a patient parameter.

27. The method of claim 21, further comprising transmitting the one or more values to a remote computer via a network interface.

* * * * *